US010695577B2

(12) United States Patent
De Taboada et al.

(10) Patent No.: US 10,695,577 B2
(45) Date of Patent: Jun. 30, 2020

(54) DEVICE AND METHOD FOR PROVIDING PHOTOTHERAPY TO THE HEART

(75) Inventors: Luis De Taboada, Carlsbad, CA (US); Jackson Streeter, Reno, NV (US)

(73) Assignee: PhotoThera, Inc., Carlsbad, CA (US)

( * ) Notice: Subject to any disclaimer, the term of this patent is extended or adjusted under 35 U.S.C. 154(b) by 0 days.

(21) Appl. No.: 10/818,947

(22) Filed: Apr. 6, 2004

(65) Prior Publication Data

US 2004/0260367 A1 Dec. 23, 2004

Related U.S. Application Data

(63) Continuation-in-part of application No. 10/328,153, filed on Dec. 23, 2002, now abandoned.

(60) Provisional application No. 60/549,679, filed on Mar. 3, 2004, provisional application No. 60/410,080, filed on Sep. 12, 2002, provisional application No. 60/353,638, filed on Jan. 31, 2002, provisional application No. 60/345,177, filed on Dec. 21, 2001.

(51) Int. Cl.
*A61N 5/06* (2006.01)
*A61N 5/067* (2006.01)

(52) U.S. Cl.
CPC ...... *A61N 5/0601* (2013.01); *A61N 2005/067* (2013.01); *A61N 2005/0652* (2013.01); *A61N 2005/0659* (2013.01)

(58) Field of Classification Search
CPC .......... A61N 5/0601; A61N 2005/0652; A61N 2005/067; A61N 2005/0659; A61N 2005/0609
USPC ................ 128/898; 607/88–93; 606/3, 9–15, 606/192–194; 600/428
See application file for complete search history.

(56) References Cited

U.S. PATENT DOCUMENTS

| 3,576,185 | A | * | 4/1971 | Schulz et al. .................. 600/27 |
| 3,375,755 | A | | 5/1973 | Eggleton et al. |
| 3,810,367 | A | | 5/1974 | Peterson |
| 4,315,514 | A | | 2/1982 | Drewes et al. |
| 4,343,301 | A | | 8/1982 | Indech |
| 4,539,987 | A | | 9/1985 | Nath et al. |
| 4,630,273 | A | | 12/1986 | Inoue et al. |

(Continued)

FOREIGN PATENT DOCUMENTS

| DE | 32 00 584 A1 | 7/1983 |
| DE | 42 13 053 A | 10/1993 |

(Continued)

OTHER PUBLICATIONS

US 6,344,051 B1, 02/2002, Dumoulin-White et al. (withdrawn)

(Continued)

*Primary Examiner* — Christopher A Flory
*Assistant Examiner* — Vynn V Huh
(74) *Attorney, Agent, or Firm* — Fish & Richardson P.C.

(57) ABSTRACT

A method for treating a patient's heart is provided. The method includes providing a light source which emits light having an initial power density. The method further includes positioning the light source relative to the patient's heart with intervening tissue of the patient between the light source and the patient's heart. The method further includes directing light onto cardiac tissue of the patient's heart from the light source through the intervening tissue without damaging the intervening tissue. The cardiac tissue is irradiated by an efficacious power density of light for an efficacious period of time.

31 Claims, 20 Drawing Sheets

(56) References Cited

U.S. PATENT DOCUMENTS

| | | | |
|---|---|---|---|
| 4,633,872 A | 1/1987 | Chaffee et al. | |
| 4,669,466 A | 6/1987 | L'Esperance | |
| 4,798,215 A | 1/1989 | Turner | |
| 4,836,203 A | 6/1989 | Muller et al. | |
| 4,846,196 A | 7/1989 | Wiksell et al. | |
| 4,930,504 A | 6/1990 | Diamantopoulos et al. | |
| 4,951,482 A | 8/1990 | Gilbert | |
| 4,951,653 A | 8/1990 | Fry et al. | |
| 4,966,144 A | 10/1990 | Rochkind et al. | |
| 5,029,581 A | 7/1991 | Kaga et al. | |
| 5,037,374 A | 8/1991 | Carol | |
| 5,053,006 A | 10/1991 | Watson | |
| 5,054,470 A | 10/1991 | Fry et al. | |
| 5,150,704 A | 9/1992 | Tatebayashi et al. | |
| 5,167,610 A * | 12/1992 | Kitado et al. | 600/26 |
| 5,259,380 A | 11/1993 | Mendes et al. | |
| 5,265,598 A | 11/1993 | Searfoss et al. | |
| 5,267,294 A | 11/1993 | Kuroda et al. | |
| 5,282,797 A | 2/1994 | Chess | |
| 5,304,212 A | 4/1994 | Czeisler et al. | |
| 5,358,503 A | 10/1994 | Bertwell et al. | |
| 5,368,555 A | 11/1994 | Schwartz | |
| 5,401,270 A | 3/1995 | Muller et al. | |
| 5,405,368 A | 4/1995 | Eckhouse | |
| 5,441,495 A | 8/1995 | Liboff et al. | |
| 5,445,146 A | 8/1995 | Bellinger | |
| 5,445,608 A | 8/1995 | Chen et al. | |
| 5,464,436 A | 11/1995 | Smith | |
| 5,474,528 A | 12/1995 | Meserol | |
| 5,501,655 A | 3/1996 | Rolt et al. | |
| 5,511,563 A | 4/1996 | Diamond | |
| 5,540,737 A | 7/1996 | Fenn | |
| 5,580,550 A | 12/1996 | Gough et al. | |
| 5,580,555 A | 12/1996 | Schwartz | |
| 5,601,526 A | 2/1997 | Chapelon et al. | |
| 5,616,140 A | 4/1997 | Prescott | |
| 5,621,091 A | 4/1997 | Kunkel et al. | |
| 5,622,168 A | 4/1997 | Keusch et al. | |
| 5,627,870 A | 5/1997 | Kopecky | |
| 5,640,978 A | 6/1997 | Wong | |
| 5,643,334 A | 7/1997 | Eckhouse et al. | |
| 5,683,436 A | 11/1997 | Mendes et al. | |
| 5,709,645 A | 1/1998 | Siever | |
| 5,720,894 A | 2/1998 | Neev et al. | |
| 5,728,090 A | 3/1998 | Martin et al. | |
| 5,735,844 A | 4/1998 | Anderson et al. | |
| 5,755,752 A | 5/1998 | Segal | |
| 5,762,867 A | 6/1998 | D'Silva | |
| 5,769,878 A | 6/1998 | Kamei | |
| 5,800,479 A | 9/1998 | Thiberg | |
| 5,817,008 A | 10/1998 | Rafert et al. | |
| 5,830,208 A | 11/1998 | Muller | |
| 5,842,477 A | 12/1998 | Naughton et al. | |
| 5,843,073 A | 12/1998 | Sinofsky | |
| 5,849,585 A | 12/1998 | Mather et al. | |
| 5,879,376 A | 3/1999 | Miller | |
| 5,902,741 A | 5/1999 | Purchio et al. | |
| 5,928,207 A | 7/1999 | Pisano et al. | |
| 5,928,945 A | 7/1999 | Seliktar et al. | |
| 5,951,596 A | 9/1999 | Bellinger | |
| 5,954,762 A | 9/1999 | Di Mino et al. | |
| 5,958,761 A | 9/1999 | Yogev et al. | |
| 5,983,141 A | 11/1999 | Sluijter et al. | |
| 5,989,245 A * | 11/1999 | Prescott | 606/14 |
| 5,993,442 A | 11/1999 | Omori | |
| 6,015,404 A | 1/2000 | Altshuler et al. | |
| 6,027,495 A | 2/2000 | Miller | |
| RE36,634 E | 3/2000 | Ghaffari | |
| 6,033,431 A | 3/2000 | Segal | |
| 6,042,531 A | 3/2000 | Holcomb | |
| 6,045,575 A | 4/2000 | Rosen et al. | |
| 6,046,046 A | 4/2000 | Hassanein | |
| 6,059,820 A | 5/2000 | Baronov | |
| 6,060,306 A | 5/2000 | Flatt et al. | |
| 6,063,108 A | 5/2000 | Salansky et al. | |
| 6,084,242 A | 7/2000 | Brown et al. | |
| 6,100,290 A | 8/2000 | Levy et al. | |
| 6,107,325 A | 8/2000 | Chan et al. | |
| 6,107,608 A | 8/2000 | Hayes | |
| 6,112,110 A | 8/2000 | Wilk | |
| 6,117,128 A | 9/2000 | Gregory | |
| 6,129,748 A | 10/2000 | Kamei | |
| 6,143,878 A | 11/2000 | Koopman et al. | |
| 6,146,410 A | 11/2000 | Nagypal et al. | |
| 6,149,679 A | 11/2000 | Di Mino et al. | |
| 6,156,028 A | 12/2000 | Prescott | |
| 6,179,771 B1 | 1/2001 | Mueller | |
| 6,187,210 B1 | 2/2001 | Lebouitz et al. | |
| 6,198,958 B1 | 3/2001 | Ives et al. | |
| 6,210,317 B1 | 4/2001 | Bonlie | |
| 6,213,998 B1 | 4/2001 | Shen et al. | |
| 6,214,035 B1 | 4/2001 | Streeter | |
| 6,221,095 B1 | 4/2001 | Van Zuylen et al. | |
| 6,235,015 B1 | 5/2001 | Mead et al. | |
| 6,238,424 B1 | 5/2001 | Thiberg | |
| 6,238,425 B1 | 5/2001 | Thiberg | |
| 6,264,649 B1 | 7/2001 | Whitcroft et al. | |
| 6,267,779 B1 | 7/2001 | Gerdes | |
| 6,267,780 B1 | 7/2001 | Streeter | |
| 6,273,884 B1 | 8/2001 | Altshuler et al. | |
| 6,273,905 B1 | 8/2001 | Streeter | |
| 6,277,974 B1 | 8/2001 | Lo et al. | |
| 6,290,713 B1 | 9/2001 | Russell | |
| 6,290,714 B1 | 9/2001 | Streeter | |
| 6,312,451 B1 | 11/2001 | Streeter | |
| 6,344,050 B1 | 2/2002 | Chen | |
| 6,358,272 B1 | 3/2002 | Wilden | |
| 6,363,285 B1 | 3/2002 | Wey | |
| 6,364,907 B1 | 4/2002 | Obochi et al. | |
| 6,379,295 B1 | 4/2002 | Woo | |
| 6,391,023 B1 | 5/2002 | Weber et al. | |
| 6,395,016 B1 | 5/2002 | Oron et al. | |
| 6,397,107 B1 | 5/2002 | Lee et al. | |
| 6,402,678 B1 | 6/2002 | Fischell et al. | |
| 6,421,562 B1 | 7/2002 | Ross | |
| 6,432,101 B1 | 8/2002 | Weber et al. | |
| 6,436,094 B1 | 8/2002 | Reuter | |
| 6,440,121 B1 | 8/2002 | Weber et al. | |
| 6,443,974 B1 | 9/2002 | Oron et al. | |
| 6,443,977 B1 | 9/2002 | Jaillet | |
| 6,443,978 B1 | 9/2002 | Zharov | |
| 6,458,120 B1 | 10/2002 | Shen et al. | |
| 6,471,716 B1 | 10/2002 | Pecukonis | |
| 6,494,900 B1 | 12/2002 | Salansky et al. | |
| 6,508,813 B1 | 1/2003 | Altshuler | |
| 6,511,475 B1 | 1/2003 | Altshuler et al. | |
| 6,514,220 B2 | 2/2003 | Melton, Jr. et al. | |
| 6,530,920 B1 | 3/2003 | Whitcroft et al. | |
| 6,537,301 B1 | 3/2003 | Kamei | |
| 6,537,302 B1 | 3/2003 | Thiberg | |
| 6,537,304 B1 | 3/2003 | Oron | |
| 6,551,308 B1 | 4/2003 | Muller et al. | |
| 6,571,735 B1 | 6/2003 | Wilkinson | |
| 6,602,245 B1 | 8/2003 | Thiberg | |
| 6,602,274 B1 | 8/2003 | Chen | |
| 6,602,275 B1 | 8/2003 | Sullivan | |
| 6,632,219 B1 | 10/2003 | Baronov et al. | |
| 6,638,272 B2 | 10/2003 | Cho et al. | |
| 6,653,618 B2 | 11/2003 | Zenzie | |
| 6,663,620 B2 | 12/2003 | Altshuler et al. | |
| 6,663,659 B2 | 12/2003 | McDaniel et al. | |
| 6,679,877 B2 | 1/2004 | Ota et al. | |
| 6,685,702 B2 | 2/2004 | Quijano et al. | |
| 6,689,062 B1 * | 2/2004 | Mesallum | 606/192 |
| 6,692,517 B2 | 2/2004 | Cho et al. | |
| 6,702,837 B2 | 3/2004 | Gutwein | |
| 6,733,492 B2 | 5/2004 | Ota et al. | |
| 6,770,069 B1 | 8/2004 | Hobart et al. | |
| 6,817,997 B2 | 11/2004 | Furuno et al. | |
| 6,832,111 B2 | 12/2004 | Tu et al. | |
| 6,866,678 B2 | 3/2005 | Shenderova et al. | |
| 6,872,221 B2 | 3/2005 | Lytle | |
| 6,878,144 B2 | 4/2005 | Altshuler et al. | |
| 6,896,693 B2 | 5/2005 | Sullivan | |

(56) References Cited

U.S. PATENT DOCUMENTS

| | | | |
|---|---|---|---|
| 6,918,922 | B2 | 7/2005 | Oron |
| 6,921,413 | B2 | 7/2005 | Mahadevan-Jansen et al. |
| 6,974,224 | B2 | 12/2005 | Thomas-Benedict |
| 6,974,450 | B2 | 12/2005 | Weber et al. |
| 6,974,451 | B2 | 12/2005 | Altshuler et al. |
| 6,976,985 | B2 | 12/2005 | Altshuler et al. |
| 7,037,326 | B2 | 5/2006 | Lee |
| 7,051,738 | B2 | 5/2006 | Oron et al. |
| 7,070,611 | B2 | 7/2006 | Biel |
| 7,077,840 | B2 | 7/2006 | Altshuler et al. |
| 7,081,128 | B2 | 7/2006 | Hart et al. |
| 7,083,610 | B1 | 8/2006 | Murray et al. |
| 7,100,615 | B1 | 9/2006 | Kert |
| 7,101,384 | B2 | 9/2006 | Thomas-Benedict |
| 7,107,997 | B1 | 9/2006 | Moses et al. |
| 7,139,612 | B2 | 11/2006 | Chow et al. |
| 7,150,710 | B2 | 12/2006 | Haber et al. |
| 7,217,266 | B2 | 5/2007 | Anderson et al. |
| 7,220,254 | B2 | 5/2007 | Altshuler et al. |
| 7,282,060 | B2 | 10/2007 | DeBenedictis et al. |
| 7,288,108 | B2 | 10/2007 | DiMauro et al. |
| 7,311,722 | B2 | 12/2007 | Larsen |
| 7,311,723 | B2 | 12/2007 | Seibel et al. |
| 7,351,252 | B2 | 4/2008 | Altshuler et al. |
| 7,351,253 | B2 | 4/2008 | DiMauro et al. |
| 7,402,167 | B2 | 7/2008 | Nemenov et al. |
| 2001/0044623 | A1 | 11/2001 | Chen |
| 2002/0029071 | A1 | 3/2002 | Whitehurst |
| 2002/0068927 | A1 | 6/2002 | Prescott |
| 2002/0087205 | A1 | 7/2002 | Chen |
| 2002/0123781 | A1 | 9/2002 | Shanks et al. |
| 2002/0156371 | A1* | 10/2002 | Hedlund et al. ............... 600/428 |
| 2002/0198575 | A1 | 12/2002 | Sullivan |
| 2003/0125782 | A1 | 7/2003 | Streeter |
| 2003/0144712 | A1 | 7/2003 | Streeter |
| 2003/0181961 | A1 | 9/2003 | Kamei |
| 2003/0212442 | A1* | 11/2003 | Streeter ................ A61N 5/0601 607/88 |
| 2003/0216797 | A1 | 11/2003 | Oron |
| 2004/0014199 | A1 | 1/2004 | Streeter |
| 2004/0044384 | A1 | 3/2004 | Leber et al. |
| 2004/0132002 | A1 | 7/2004 | Streeter |
| 2004/0138727 | A1 | 7/2004 | Taboada et al. |
| 2004/0220513 | A1 | 11/2004 | Streeter |
| 2004/0260367 | A1 | 12/2004 | De Taboada et al. |
| 2005/0009161 | A1 | 1/2005 | Streeter |
| 2005/0216072 | A1 | 3/2005 | Mahadevan-Jansen et al. |
| 2005/0107851 | A1 | 5/2005 | Taboada et al. |
| 2005/0203595 | A1 | 9/2005 | Oron |
| 2006/0184214 | A1 | 2/2006 | McDaniel |
| 2006/0155348 | A1 | 7/2006 | deCharms |
| 2006/0167532 | A1 | 7/2006 | Parker |
| 2007/0129778 | A1 | 1/2007 | Dougal |
| 2007/0162093 | A1 | 7/2007 | Porter et al. |
| 2007/0219605 | A1 | 9/2007 | Yaroslavsky et al. |
| 2007/0260295 | A1 | 11/2007 | Chen et al. |
| 2007/0288072 | A1 | 12/2007 | Pascual-Leone et al. |
| 2008/0051858 | A1 | 2/2008 | Haber et al. |
| 2008/0077199 | A1 | 3/2008 | Shefi et al. |
| 2008/0103562 | A1 | 5/2008 | Anders et al. |
| 2008/0140164 | A1 | 6/2008 | Oberreiter et al. |

FOREIGN PATENT DOCUMENTS

| | | |
|---|---|---|
| DE | 295 15 096 U1 | 1/1996 |
| EP | 0 130 950 | 11/1990 |
| EP | 0 763 371 A2 | 3/1997 |
| EP | 0 783 904 A2 | 7/1997 |
| EP | 1226787 A2 | 7/2002 |
| JP | 04023634 | 2/1992 |
| WO | WO 96/36396 | 11/1996 |
| WO | WO 98/04321 | 2/1998 |
| WO | WO 98/22573 | 5/1998 |
| WO | WO 98/33556 | 8/1998 |
| WO | PCT/CA99/00156 | 8/1999 |
| WO | WO 99/42178 | 8/1999 |
| WO | WO 99/62599 A1 | 12/1999 |
| WO | WO 00/35534 | 6/2000 |
| WO | PCT/US02/36808 | 5/2003 |
| WO | PCT/US03/00747 | 7/2003 |
| WO | PCT/US2004/029724 | 9/2004 |
| WO | PCT/US0025/004873 | 2/2005 |
| WO | PCT/US2005/004873 | 2/2005 |
| WO | WO 2005/025672 A1 | 3/2005 |
| WO | WO 06/105254 | 10/2006 |

OTHER PUBLICATIONS

Dobson, J., et al., et al., Theory and Applications of a Magnetic Force Bioreactor, *European Cells and Materials*, vol. 4, Suppl. 2, 2002 (pp. 42-43).

Mester, E., et al., Effect of Laser Rays on Wound Healing, *The American Journal of Surgery*, vol. 122, Oct. 1971, pp. 532-535.

Mochizuki-Oda, Noriko, et al., Effects of near-infra-red laser irradiated on adenosine triphosphate and adenosine diphosphate contents of rat brain tissue, *Neuroscience Letters 323*, May 3, 2002, pp. 207-210.

Park, James L., Ph.D., et al., Mechanisms of Myocardial Reperfusion Injury, *The Annals of Thoracic Surgery*, Official Journal of the Society of Thoracic Surgeons and the Southern Thoracic Surgical Association, vol. 68, No. 5, Nov. 1999, pp. 1905-1912.

Toricelli, P., et al., Laser Biostimulation of cartilage: in vitro evaluation, *Biomed Pharmacother* 2001, vol. 55, pp. 117-120.

Agov, B.S., et al., On the mechanism of therapeutic action of helium-neon laser in ischemic heart disease, *KLIN MED (Mosc)*, 1985, pp. 102-105 (Abstract only).

Basford, Jeffrey R., M.D., Ph.D., Lasers in Orthopedic Surgery, *Laser Therapy: Scientific Basis and Clinical Role*, vol. 16, No. 5, May 1993, pp. 541-547.

Gordon, G.A., The use of low power lasers in sports medicine, *Clinical Sports Medicine*, vol. 2, 1990, pp. 53-61.

Olesin, Al, et al., Laser irradiation of venous blood for production of reperfusion syndrome in myocardial infarction, *Patologisheskaia fiziologiia*, 1992 (Abstract only).

The Efficacy of Laser Therapy for Musculoskeletal and Skin Disorders: A Criteria-Based Meta-analysis of Randomized Clinical Trials, *Physical Therapy*, vol. 72, No. 7, Jul. 1992, pp. 483/13-491/21.

Smith, Kendric C., The Photobiological Basis of Low Level Laser Radiation Therapy, *Photobiological Basis of LLLT*, pp. 19-24.

Product List, Tho, lllt, LLLT, Low Level Laser Therapy, Laz., http://www.thorlaser.com/prodlist/index.html, Oct. 6, 1999, pp. 1-4.

Specifications, Thor, lllt, LLLT, Low Level Laser Therapy, low level laser therapy, http://www.thorlaser.com/specs, Oct. 6, 1999, pp. 1-2.

100mW, Thor, lllt, LLLT, Low Level Laser Therapy, low level laser therapy, Lazer, Thorl., http://www.thorlaser.com/_specs/_100m_W.html, Oct. 6, 1999; p. 1.

200mW, Thor, lllt, LLLT, Low Level Laser Therapy, low level laser therapy, Lazer, Thorl., http://www.thorlaser.com/_specs/200m_W.html, Oct. 6, 1999, p. 1.

500mW, Thor, lllt, LLLT, Low Level Laser Therapy, low level laser therapy, Lazer, Thorl., http://www.thorlaser.com/_specs/500m_W.html, Oct. 6, 1999, p. 1.

200mW, Thor, lllt, LLLT, Low Level Laser Therapy, low level laser therapy, Laser, Thorl., http://www.thorlaser.com/_specs/200m_W650nm.html, Oct. 6, 1999, p. 1.

680nm Probe, Thor, lllt, LLLT, Low Level Laser Therapy, low level laser therapy, Laser, http://www.thorlaser.com/_specs/680.html, Oct. 6, 1999, p. 1.

Arvidsson, Andreas, et al., Neuronal replacement from endogenous precursors in the adult rat brain after stroke, *Nature Medicine*; vol. 8, No. 9; Sep. 2000; pp. 963-970.

Asahi, Minoru, et al., Expression of interleukin B converting enzyme gene family and Bcl-2 gene family in the rat brain following permanent occlusion of the middle cerebral artery, *Journal of Cerebral Blood Flow & Metabolism*, vol. 17, No. 1; Jan. 1997; pp. 11-18.

(56) References Cited

OTHER PUBLICATIONS

Brazzle, John, et al., Active Microneedles with Integrated Functionality, *Technical Digest of the 2000 Solid-State Sensor and Actuator Workshop*, Department of Bioengineering, University of Utah, 2000; pp. 1-5.
Brill, G.E. et al., Modifying influence of low level laser irradiation on the relationships in endothelial cell—blood platelet system, $10^{th}$ Congress of the European Society for Photobiology, Vienna, Austria; 2003.
Byrnes, K., et al., Light Therapy Promotes Axonal Regeneration After Acute Spinal Cord Injury in Adult Rats, Program No. 275.2, Society for Neuroscience, 2003, Abstract.
Cohen, Michael A., Method of Forming Microneedle and other Micron-Scale Transdermal, Office of Technology Licensing, University of California, Berkeley, http://otl.berkeley.edu/technology/inventiondetail.php/1000335, Abstract.
Dirnagl, Ulrich, et al., Pathobiology of ischemic stroke an integrated review, *TINS*, vol. 22, No. 9; 1999; pp. 391-397.
Eells, J.T., et al., *Proceedings National Academy of Science, PNAS*, vol. 100, No. 6; 2003; pp. 3439-3444.
Elimadi, Aziz, et al., Trimetazidine Counteracts the Hepatic Injury Associated with Ischemia-Reperfusion by Preserving Mitochondrial Function, *Journal of Pharmacology and Experimental Therapeutics*, vol. 286, No. 1; 1998; pp. 23-28.
Gage, F., Brain, Repair Yourself, *Scientific American*, 2003; Sep.; pp. 47-53.
Gasparyan, Levon V., et al., Low Level Laser Therapy of Male Genital Tract Chronic Inflammations, WALT 2-nd Congress (Kansas City, USA); 1998; pp. 1-2.
Gasparyan, Levon V., et al., The influence of LED irradiation at different wavelengths on functional activity of blood, $10^{th}$ Congress of the European Society for Photobiology, Vienna, Austria; 2003; (one pages).
Gasparyan, Levon, et al., The influence of LED irradiation at different wavelengths with antioxidants on functional activity of blood platelets, 2003, Laser, Florence (one page).
Gasparyan, Levon V., Investigation of Sensations, Associated with Laser Blood Irradiation, WALT 2-nd Congress (Kansas City, USA), 1998 (two pages).
Iadecola, C., et al., Inhibition of inducible nitric oxide synthase ameliorates ischemic damage, *Am. J. Physiol.*, vol. 268; 1995; pp. R286-R292.
Karu, Tiina I., et al., Effects of Low-Power Light on Biological Systems V, *Progress in Biomedical Optics and Imaging*, vol. 1, No. 30, Proceedings of SPIE, vol. 4159; Jul. 7, 2000; pp. 1-17.
Karu, T.I., Low power laser therapy, in Biomedical Photonics Handbook, Ch. 48, Editor-in-chief Tuan Vo-Dinh, Boca Raton: CRC Press; 2003; 30 pages.
Karu, T., Mechanisms of interaction of monochromatic visible light with cells, Proc. SPIE; vol. 2630; 1995; pp. 2-9.
Karu, Tiina I., Mechanisms of Low-Power Laser Light Action on Cellular Level, Proc. SPIE vol. 4159, Effects of Low-Power Light on Biological Systems V, Ed. Rachel Lubart; 2000; pp. 1-17.
Karu, T., Photobiological Fundamentals of Low Power Laser Therapy, *IEEE Journal of Quantum Electronics*; vol. QE-23, No. 10; Oct. 1987; pp. 1703-1717.
Leung, Mason C.P., et al., Treatment of Experimentally Induced Transient Cerebral Ischemia with Low Energy Laser Inhibits Nitric Oxide Synthase Activity and Up-Regulates the Expression of Transforming Growth Factor-Beta 1, *Lasers in Surgery and Medicine*; vol. 31; 2002; pp. 283-288.
Nishioka, N.S., et al., Reflection and transmission of laser light from the esophagus: the influence of incident angle; Medical Services, Massachusetts General Hospital, Boston, Abstract.
Oron, U., et al., Attenuation of infarct size in rats and dogs after myocardial infarction by low energy laser irradiation, *Lasers in Surgery and Medicine*; vol. 28; 2001; pp. 204-211.
Oron, U., et al., Low energy laser irradiation reduces formation of scar tissue after myocardial infarction in rats and dogs, Circulation 2001; 103; pp. 296-230.
Semenza, G., et al., Regulation of mammalian oxygen homeostasis by hypoxia inducible factor 1, *Ann. Rev. Cell Dev. Biol.*; vol. 15; 1999; pp. 551-578.
Stys, P., Anoxic and ischemic injury of myelinated axons in CNS white matter: from mechanistic concepts to therapeutics, *J. Cereb. Blood Flow Metab.*; vol. 18, No. 1; Jan. 1998, pp. 2-25.
Toon, John, Taking the "Ouch" Out of Needles: Arrays of Micron-Scale "Microneedles" Offer New Technique for Drug Delivery, *Georgia Tech Research News*, Jun. 22, 1998 (three pages).
Tuchin, V., Tissue Optics: Light Scattering Methods and Instruments for Medical Diagnosis, SPIE Press; Bellingham, WA; 2000; pp. 3-11.
Tunér, J., et al., Laser Therapy Clinical Practice and Scientific Background, A guide for research scientists, doctors, dentists, veterinarians and other interested parties within the medical field, Prima Books AB, 2002, pp. 62-114; 134-135; 149-151; 185; 334-364.
Van Breugen, Hans H.F.I. et al., Power Density and Exposure of He—Ne Laser Irradiation Are More Important Than Total Energy Dose in Photo-Blomodulation of Human Fibroblasts In Vitro, *Lasers in Surgery and Medicine*; vol. 12; 1992; pp. 528-537.
Wong-Riley, M.T., et al., Light-emitting diode treatment reverses the effect of TTX on cytochrome oxidase in neurons, *NeuroReport*, vol. 12, No. 14; Oct. 2001; pp. 3033-3037.
Yaakobi et al., Long-term effect of low energy laser irradiation on infarction and reperfusion injury in the rat heart, *J. Appl. Physiol.*, vol. 90; pp. 2411-2419.
The Laser Exchange, Delivering the medicine of the future, http://www.laserexchange.co.uk/index1.htm, 42 pages, Jul. 11, 2005.
"Is LLLT Different from Ultrasound?", http://www.thorlaser.com/LLLT/is-LLLT-diff-from-ultrasound.htm. 2 pages, Oct. 13, 2004.
Gasparyan, Levon V., "Millimeter Wave Therapy," *MAL 2000*, Helsinki, Finland, 3 pages, Sep. 28-30, 2000.
Gasparyan, Levon V., "Biochemical and Biophysical Effects of Low Level Laser Irradiation," *MAL 2000*, Helsinki, Finland, 3 pages, Sep. 28-30, 2000.
Gasparyan, Levon V., "Experience of Russian (former USSR) Scientists in LLLT and UV Blood Irradiation," *MAL 2000*, Helsinki, Finland, 4 pages, Sep. 28-30, 2000.
Kreisler et al., "Effect of low-leval GaAIAs laser irradiation on the proliferation rate of human periodontal ligament fibroblasts: an in vitro study," Jounrl of Clinical Periodontology, (2003), 30:353-358.
Weiss et al., "Enhancement of muscle regeneration in the rat gastrocnemius muscle by low energy laser irradiation," Anatomy and Embryology, (1992), 186: 497-503.
Van Breugel et al. "He—Ne laser irradiation affects proliferation of cultured rat Schwann cells in a dose-dependent manner," Journal of Neurocytology, (1993), 22: 185-190.

\* cited by examiner

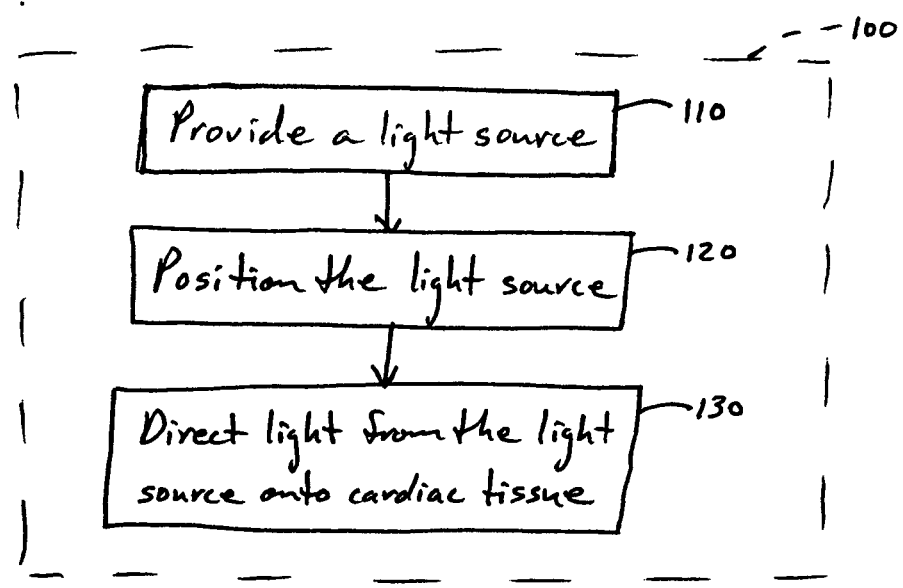

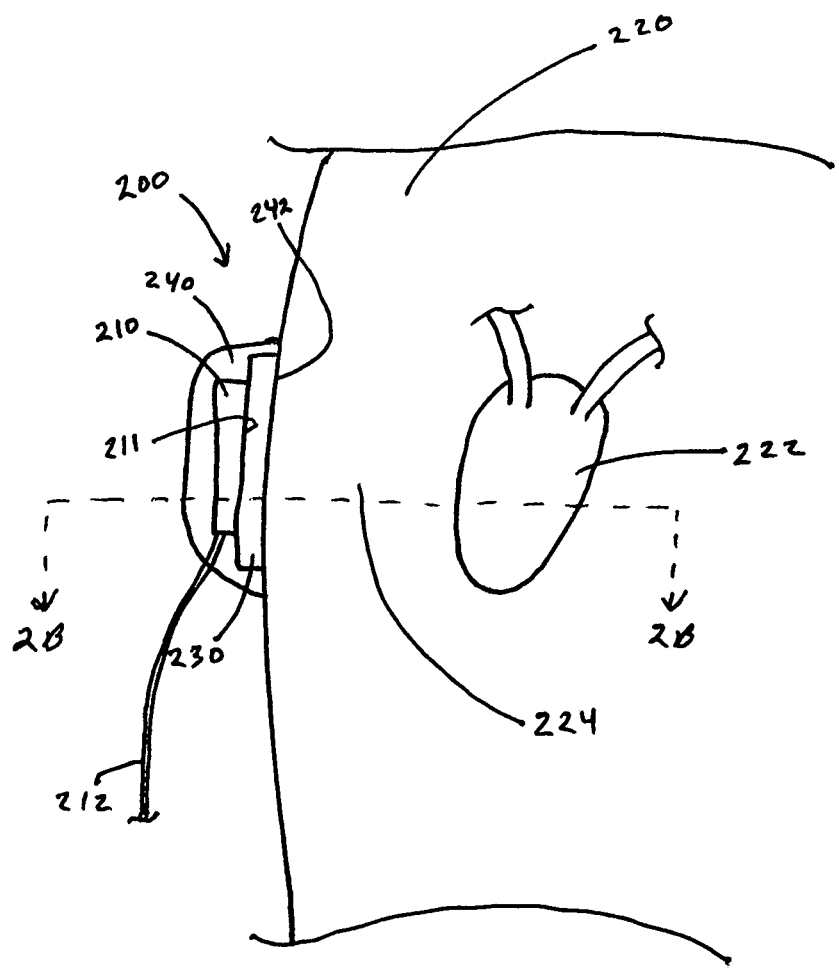

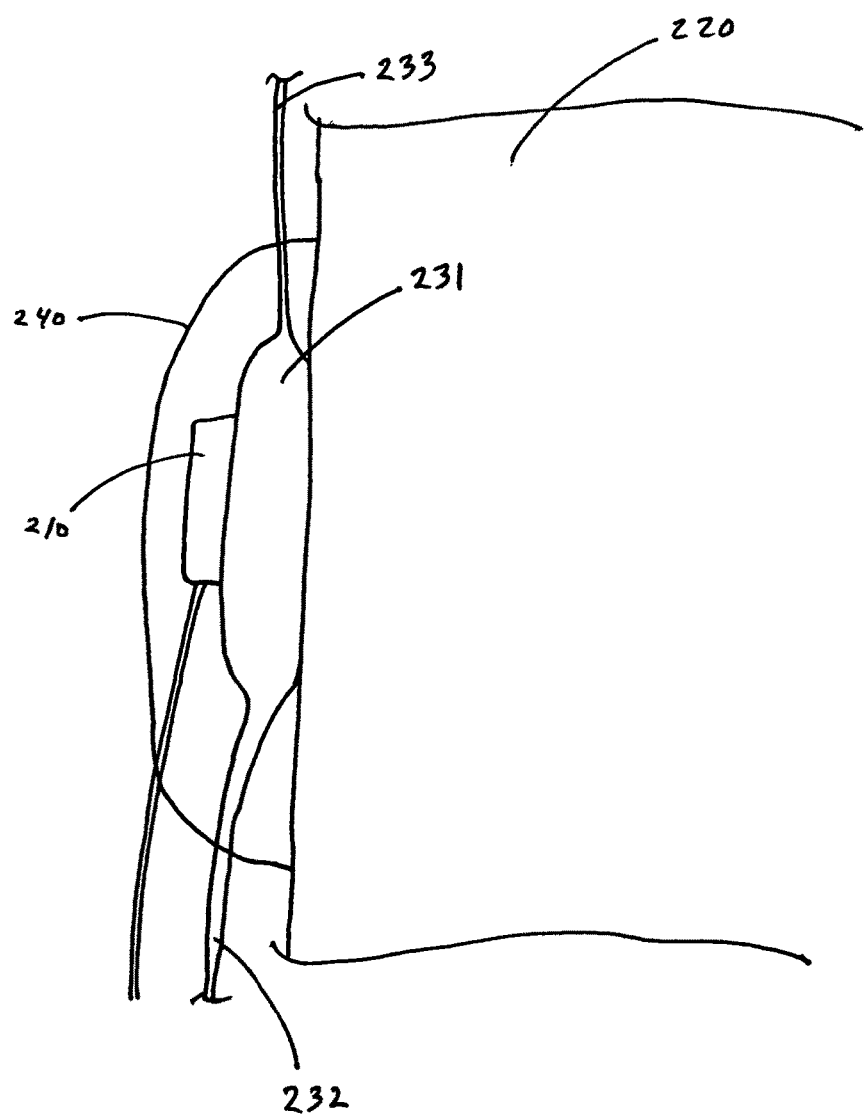

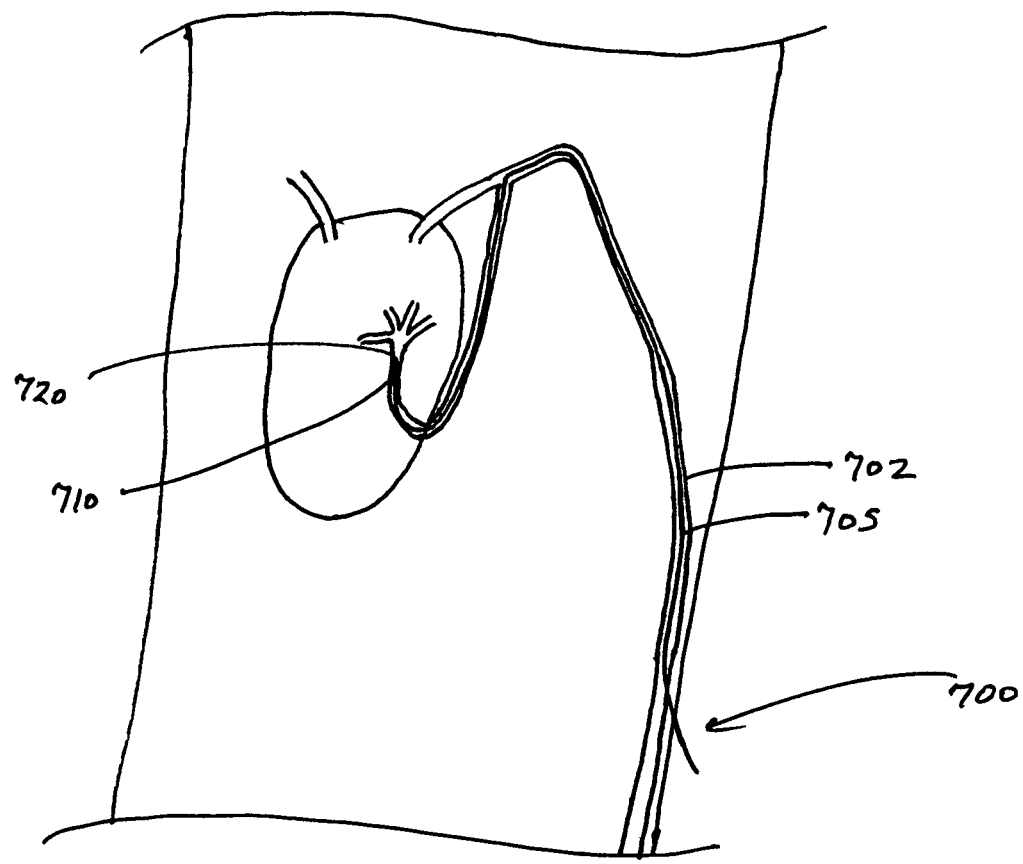

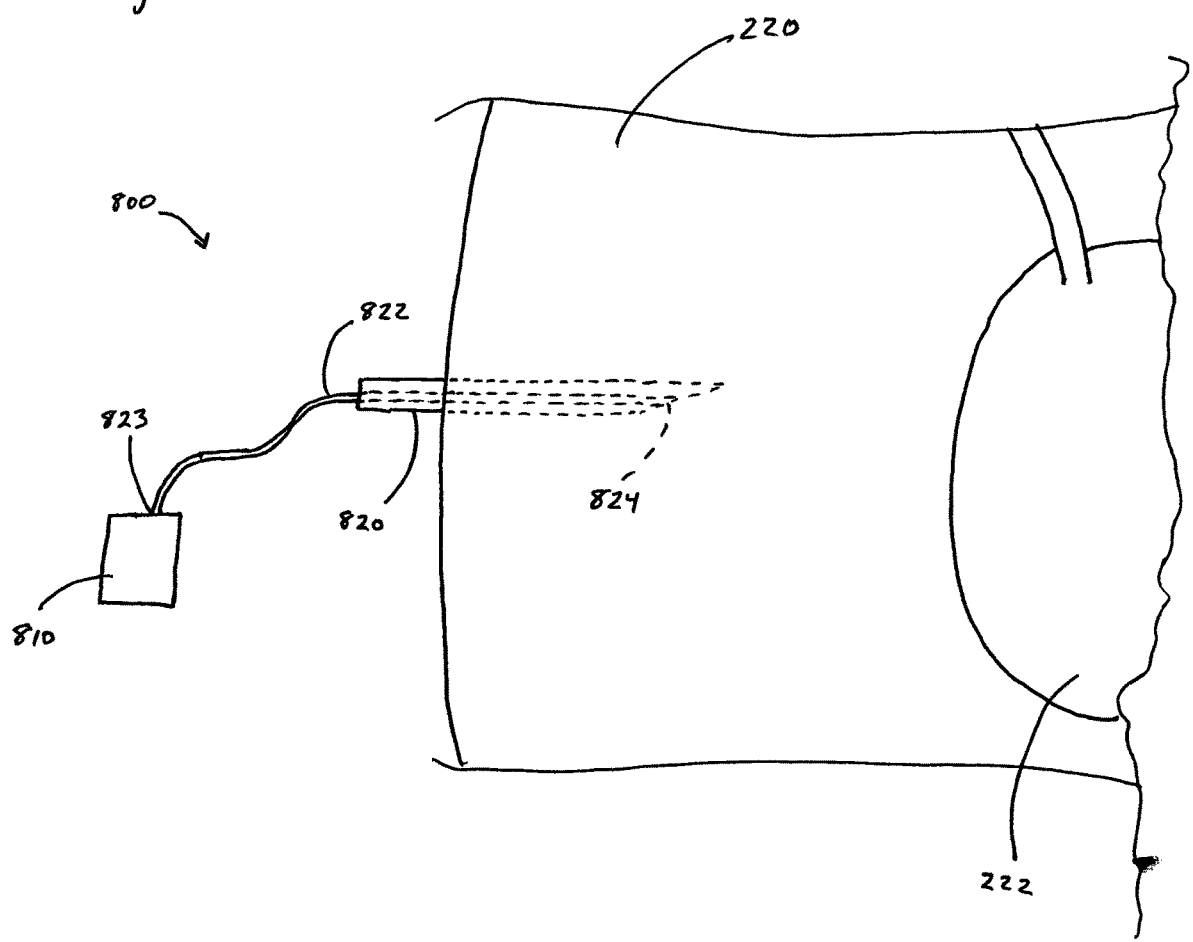

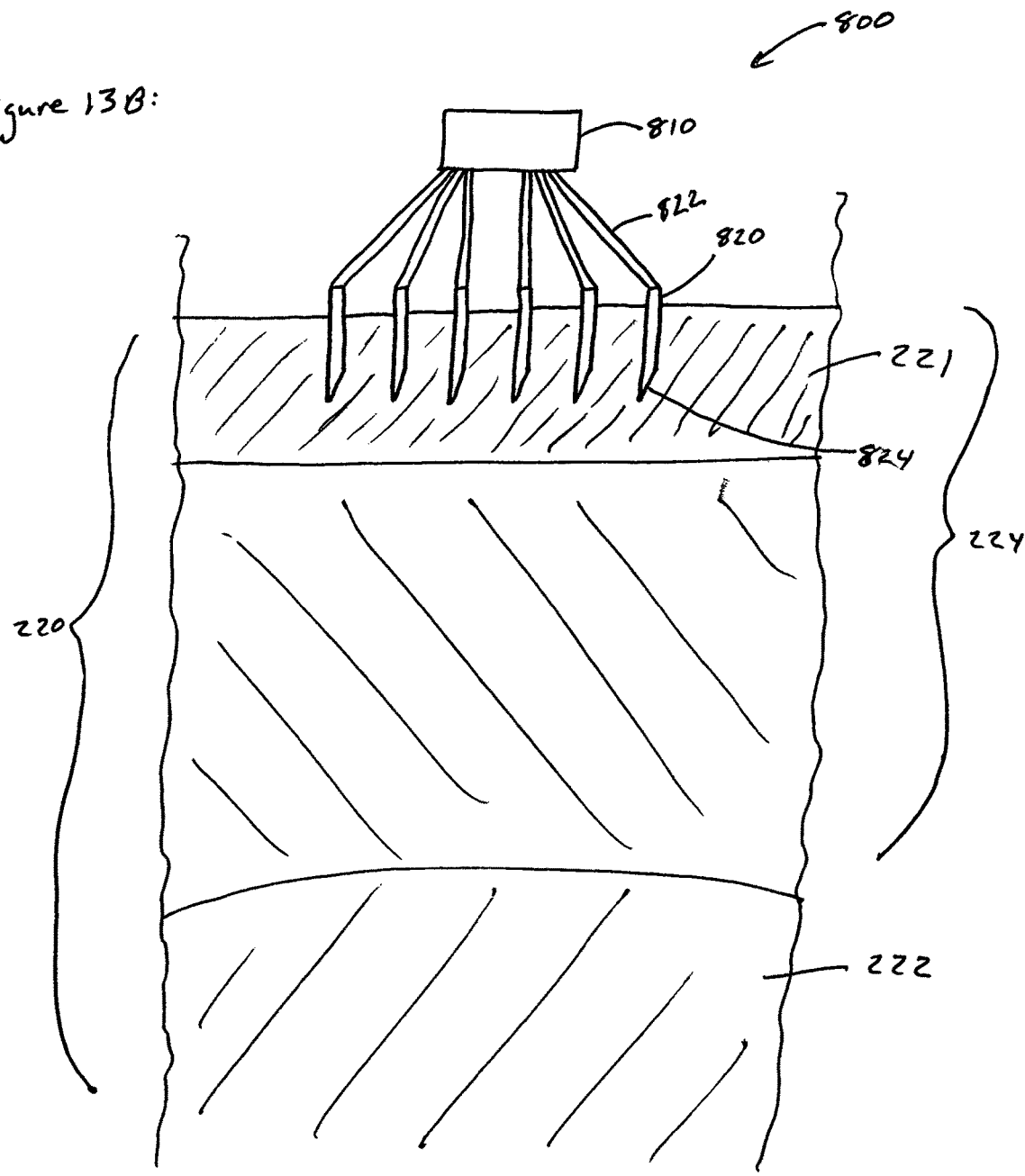

DEVICE AND METHOD FOR PROVIDING PHOTOTHERAPY TO THE HEART

CLAIM OF PRIORITY

This application is a continuation-in-part of U.S. patent application Ser. No. 10/328,153, filed Dec. 23, 2002, now abandoned which is incorporated in its entirety by reference herein and which claims benefit to U.S. Provisional Application No. 60/345,177, filed Dec. 21, 2001, U.S. Provisional Application No. 60/353,638, filed Jan. 31, 2002, and U.S. Provisional Application No. 60/410,080, filed Sep. 12, 2002, each of which is incorporated in its entirety by reference herein. This application also claims benefit to U.S. Provisional Application No. 60/549,679, filed Mar. 3, 2004, which is incorporated in its entirety by reference herein.

BACKGROUND OF THE INVENTION

Field of the Invention

The present invention relates in general to phototherapy, and more particularly, to novel apparatuses and methods for phototherapy of cardiac tissue.

Description of the Related Art

Myocardial ischemia refers to the condition of oxygen deprivation in heart muscle ("myocardium") that is produced by some imbalance in the myocardial oxygen supply-demand relationship. Myocardial infarction ("MI"), also known as "heart attack", refers to the death of cells in an area of heart muscle as a result of oxygen deprivation due to obstruction of the blood supply, typically due to occlusion of one or more coronary arteries or branches. Occlusion usually stems from clots that form upon the sudden rupture of an atheromatous plaque through the sublayers of a blood vessel, or when the narrow, roughened inner lining of a sclerosed artery leads to complete thrombosis. Approximately 1.5 million myocardial infarctions (MIs) occur annually, and nearly 500,000 deaths result from ischemic heart disease. The United States alone loses billions of dollars annually to medical care and lost productivity due to cardiovascular disease including myocardial infarction.

Treatment after MI depends on the extent to which the cells have been deprived of oxygen. Complete oxygen deprivation produces a zone of infarction in which cells die and the tissue becomes necrotic, with irretrievable loss of function. However, immediately surrounding the area of infarction is a less seriously damaged region of tissue, the zone of ischemia, in which cells have not been irretrievably damaged by complete lack of oxygen but instead are merely weakened and at risk of dying. If adequate collateral circulation develops, the extended zone may regain function within 2 to 3 weeks. The zone of infarction and the zone of ischemia, are both identifiable using standard diagnostic techniques such as electrocardiography, echocardiography and radionuclide testing.

Therapeutic strategies in treating MI are directed at reducing the final extent of the infarcted region by preserving viable tissue and if possible retrieving surviving but at-risk cells. Known treatment methods for myocardial infarction include surgical interventions and pharmacologic treatments. A combination of therapeutic approaches is sometimes advisable. Selection of the appropriate therapy depends on a number of factors, including the degree of coronary artery occlusion, the extent of existing damage if any, and fitness of the patient for surgery. Surgical interventions include coronary artery bypass surgery and percutaneous coronary procedures such as angioplasty, artherectomy and endarterectomy. Pharmacologic agents for treating MI include inhibitors of angiotensin converting enzyme (ACE) such as captopril, quinapril and ramipril, thrombolytic agents including aspirin, streptokinase, t-PA and anistreplase, β-adrenergic anatagonists, $Ca^{++}$ channel blockers, and organic nitrates such as nitroglycerin. However, surgical interventions are invasive and can increase the risk of stroke, and pharmacologic agents carry the risk of eliciting serious adverse side effects and immune responses.

High energy laser radiation is now well accepted as a surgical tool for cutting, cauterizing, and ablating biological tissue. High energy lasers are now routinely used for vaporizing superficial skin lesions and, and for making deep cuts. Examples of such procedures include transmyocardial laser revascularization (TMLR) and percutaneous transmyocardial laser revascularization (PTMR). In TMLR, a laser is inserted through a chest incision and used to drill approximately 15-30 transmural channels from the epicardial to the endocardial surfaces through the left ventricular myocardium in an attempt to improve local perfusion to ichemic myocardial territories not being reached by diseased arteries. In PTMR, the laser is introduced via a catheter. Other examples include laser ablation or cauterization of cardiac tissue to stop atrial fibrillation.

For a laser to be suitable for use as a surgical laser, it must provide laser energy at a power sufficient to heat tissue to temperatures over 50° C. Power outputs for surgical lasers vary from 1-5 W for vaporizing superficial tissue, to about 100 W for deep cutting.

In contrast, low level laser therapy involves therapeutic administration of laser energy to a patient at vastly lower power outputs than those used in high energy laser applications, resulting in desirable biostimulatory effects while leaving tissue undamaged. In rat models of myocardial infarction and ischemia-reperfusion injury, low energy laser irradiation reduces infarct size and left ventricular dilation, and enhances angiogenesis in the myocardium. (See, e.g., Yaakobi et al., *J. Appl. Physiol.,* Vol. 90, pp. 2411-19 (2001)).

Against the background, a high level of interest remains in finding new and improved therapeutic methods for the treatment of myocardial infarction. In particular, a need remains for relatively inexpensive and non-invasive approaches to treating myocardial infarction that also avoid the limitations of drug therapy.

SUMMARY OF THE INVENTION

In certain embodiments, a method for treating a patient's heart is provided. The method comprises providing a light source which emits light having an initial power density. The method further comprises positioning the light source relative to the patient's heart with intervening tissue of the patient between the light source and the patient's heart. The method further comprises directing light onto cardiac tissue of the patient's heart from the light source through the intervening tissue without damaging the intervening tissue. The cardiac tissue is irradiated by an efficacious power density of light for an efficacious period of time.

In certain embodiments, a method for treating a patient's heart is provided. The method comprises introducing light of an efficacious power density onto a target area of the heart by directing light having an initial power density through intervening tissue of the patient. The light has a plurality of wavelengths, and the efficacious power density is at least 0.01 $mW/cm^2$ at the target area.

In certain embodiments, a method for treating a patient's heart following a myocardial infarction is provided. The method comprises applying low-level light therapy to the heart no earlier than about two hours following the myocardial infarction.

In certain embodiments, a method provides a cardioprotective effect in a patient having a ischemic event in the heart. The method comprises identifying a patient who has experienced an ischemic event in the heart. The method further comprises estimating the time of the ischemic event. The method further comprises commencing administration of a cardioprotective effective amount of light energy to the heart no less than about two hours following the time of the ischemic event.

In certain embodiments, a method for treating a patient's heart is provided. The method comprises directing an efficacious power density of light through intervening tissue of the patient to a target area of the heart concurrently with applying an electromagnetic field to the heart. The electromagnetic field has an efficacious field strength.

In certain embodiments, a method for treating a patient's heart is provided. The method comprises directing an efficacious power density of light through intervening tissue of the patient to a target area of the heart concurrently with applying an efficacious amount of ultrasonic energy to the heart.

In certain embodiments, a therapy apparatus for treating a patient's heart is provided. The therapy apparatus comprises a light source having an output emission area positioned to irradiate a portion of the heart with an efficacious power density and wavelength of light through intervening tissue. The therapy apparatus further comprises an element interposed between the light source and the intervening tissue. The element is configured to inhibit temperature increases at the intervening tissue caused by the light.

In certain embodiments, a therapy apparatus for treating a patient's heart is provided. The therapy apparatus comprises a light source configured to irradiate at least a portion of the heart with an efficacious power density and wavelength of light. The therapy apparatus further comprises a biomedical sensor configured to provide real-time feedback information. The therapy apparatus further comprises a controller coupled to the light source and the biomedical sensor. The controller is configured to adjust said light source in response to the real-time feedback information.

In certain embodiments, a therapy apparatus for treating a patient's heart is provided. The therapy apparatus comprises an implantable light source configured to irradiate at least a portion of the heart with an efficacious power density and wavelength of light.

In certain embodiments, a method of treating a patient's heart is provided. The method comprises implanting a light source within the patient. The method further comprises irradiating at least a portion of the heart with an efficacious power density and wavelength of light from the implanted light source.

In certain embodiments, a therapy apparatus for treating a patient's heart is provided. The therapy apparatus comprises a light source configured to irradiate at least a portion of the patient's blood with an efficacious power density and wavelength of light prior to the blood flowing to the heart.

In certain embodiments, a method of treating a patient's heart is provided. The method comprises irradiating at least a portion of the patient's blood with an efficacious power density and wavelength of light. The method further comprises allowing the irradiated blood to flow to the heart.

For purposes of summarizing the present invention, certain aspects, advantages, and novel features of the present invention have been described herein above. It is to be understood, however, that not necessarily all such advantages may be achieved in accordance with any particular embodiment of the present invention. Thus, the present invention may be embodied or carried out in a manner that achieves or optimizes one advantage or group of advantages as taught herein without necessarily achieving other advantages as may be taught or suggested herein.

BRIEF DESCRIPTION OF THE DRAWINGS

FIG. 1 is a flow diagram of a method of treating a patient's heart in accordance with embodiments described herein.

FIGS. 2A-2B schematically illustrate an embodiment of a therapy apparatus comprising a light source configured to be placed outside the patient's torso.

FIG. 3 schematically illustrates an embodiment of a therapy apparatus with an element which comprises a container coupled to an inlet conduit and an outlet conduit for the transport of a flowing material through the element.

FIG. 12 schematically illustrates an embodiment of a therapy apparatus configured to be inserted into a blood vessel of the patient.

FIG. 13A schematically illustrates an embodiment of a therapy apparatus configured to avoid a portion of intervening tissue between the therapy apparatus and the heart.

FIG. 13B schematically illustrates an embodiment of the therapy apparatus with a plurality of needles.

DETAILED DESCRIPTION OF THE PREFERRED EMBODIMENT

Figure 2B:
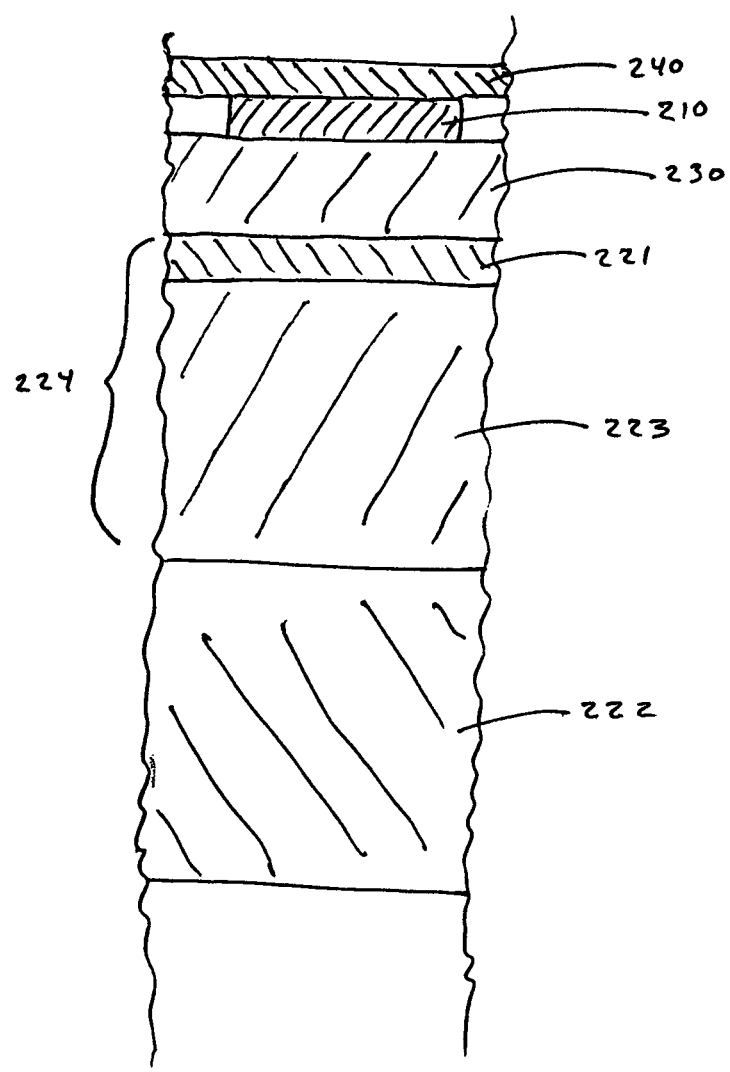

Low level light therapy ("LLLT") or phototherapy involves therapeutic administration of light energy to a patient at lower power outputs than those used for cutting, cauterizing, or ablating biological tissue, resulting in desirable biostimulatory effects while leaving tissue undamaged. For example, as described by U.S. Pat. No. 6,214,035 to Streeter, which is incorporated in its entirety by reference herein, LLLT can be used to improve cardiac microcirculation after cardiac surgeries, such as coronary bypass or angioplasty, by applying a low level of laser energy directly to a region of ischemic myocardium before closing the surgical incision.

In non-invasive or minimally-invasive phototherapy, it is desirable to apply an efficacious amount of light energy to the internal tissue to be treated without highly traumatic incisions (e.g., using light sources positioned outside the body). However, absorption of the light energy by intervening tissue can limit the amount of light energy delivered to the target tissue site, while heating the intervening tissue. In addition, scattering of the light energy by intervening tissue can limit the power density or energy density delivered to the target tissue site. Brute force attempts to circumvent these effects by increasing the power and/or power density applied to the outside surface of the body can result in damage (e.g., burning) of the intervening tissue.

Non-invasive or minimally-invasive phototherapy methods are circumscribed by setting selected treatment parameters within specified limits so as to preferably avoid damaging the intervening tissue. A review of the existing scientific literature in this field would cast doubt on whether a set of undamaging, yet efficacious, parameters could be found. However, certain embodiments, as described herein, provide devices and methods which can achieve this goal.

FIG. 1 is a flow diagram of a method 100 of treating a patient's heart in accordance with embodiments described herein. In an operational block 110, a light source is provided which emits light having an initial power density. In an operational block 120, the light source is positioned relative to the patient's heart with intervening tissue of the patient between the light source and the patient's heart. In an operational block 130, light from the light source is directed onto cardiac tissue of the patient's heart without damaging the intervening tissue. The cardiac tissue is irradiated by an efficacious power density of light for an efficacious period of time.

Providing a Light Source

The light source provided in the operational block 110 preferably generates light in the visible to near-infrared wavelength range. In certain embodiments, the light source comprises one or more laser diodes, which each provide coherent light. In embodiments in which the light from the light source is coherent, the emitted light may produce "speckling" due to coherent interference of the light. This speckling comprises intensity spikes which are created by constructive interference and can occur in proximity to the target tissue being treated. For example, while the average power density may be approximately 10 mW/cm$^2$, the power density of one such intensity spike in proximity to the cardiac tissue to be treated may be approximately 300 mW/cm$^2$. In certain embodiments, this increased power density due to speckling can improve the efficacy of treatments using coherent light over those using incoherent light for illumination of deeper tissues.

In other embodiments, the light source provides incoherent light. Exemplary light sources of incoherent light include, but are not limited to, incandescent lamps or light-emitting diodes. A heat sink can be used with the light source (for either coherent or incoherent sources) to remove heat from the light source and to inhibit temperature increases at the torso.

In certain embodiments, the light source generates light which is substantially monochromatic (i.e., light having one wavelength, or light having a narrow band of wavelengths). To maximize the amount of light transmitted to the heart, the wavelength of the light is selected in certain embodiments to be at or near a transmission peak (or at or near an absorption minimum) for the intervening tissue, which in certain embodiments corresponds to a peak in the transmission spectrum of tissue at about 820 nanometers. In certain such embodiments, the light emitted by the light source has a wavelength at which the absorption by intervening tissue is below a damaging level. In other embodiments, the wavelength of the light is preferably between about 590 nanometers and about 3000 nanometers, more preferably between about 780 nanometers and about 1064 nanometers, and most preferably between about 780 nanometers and about 840 nanometers. In still other embodiments, wavelengths of 630, 790, 800, 808, 810, 820, or 830 nanometers can be used. It has also been found that an intermediate wavelength of about 739 nanometers appears to be suitable for penetrating the intervening tissue, although other wavelengths are also suitable and may be used.

In other embodiments, the light source generates light having a plurality of wavelengths. In certain such embodiments, each wavelength is selected so as to work with one or more chromophores within the target tissue. Without being bound by theory, it is believed that irradiation of chromophores increases the production of ATP in the target tissue, thereby producing beneficial effects. In certain embodiments, the light source is configured to generate light having a first wavelength and light having a second wavelength. In certain such embodiments, the light having the first wavelength is transmitted concurrently with the light having the second wavelength to the target cardiac tissue. In certain other such embodiments, the light having the first wavelength is transmitted sequentially with the light having a second wavelength to the target cardiac tissue.

In certain embodiments, the light source includes at least one continuously emitting GaAlAs laser diode having a wavelength of about 830 nanometers. In another embodiment, the light source comprises a laser source having a wavelength of about 808 nanometers. In still other embodiments, the light source includes at least one vertical cavity surface-emitting laser (VCSEL) diode. Other light sources compatible with embodiments described herein include, but are not limited to, light-emitting diodes (LEDs) and filtered lamps.

The light source is capable of emitting light energy at a power sufficient to achieve a predetermined power density at the cardiac target tissue. The subsurface power densities are selected to be effective at producing the desired biostimulative effects on the tissue being treated. In certain embodiments, phototherapy of tissue achieved by irradiating the target cardiac tissue with average power densities of light of at least about 0.01 mW/cm$^2$ and up to about 1 W/cm$^2$. In various embodiments, the average power density at the cardiac tissue is at least about 0.01, 0.05, 0.1, 0.5, 1, 5, 10, 15, 20, 30, 40, 50, 60, 70, 80, or 90 mW/cm$^2$, respectively, depending on the desired clinical performance. In certain embodiments, the cardiac tissue is irradiated with an average power density of preferably about 0.01 mW/cm$^2$ to about 100 mW/cm$^2$, more preferably about 0.01 mW/cm$^2$ to about 50 mW/cm$^2$, and most preferably about 2 mW/cm$^2$ to about 20 mW/cm$^2$. In still other embodiments, the efficacious average power density at the cardiac tissue being irradiated is between about 10 mW/cm$^2$ and about 150 mW/cm$^2$. Other levels of power densities at the cardiac tissue being irradiated are compatible with embodiments described herein.

Taking into account the attenuation of energy as it propagates from the skin surface, through body tissue, bone, and fluids, to the subdermal target tissue, initial average power densities preferably between about 10 mW/cm$^2$ to about 10 W/cm$^2$, or more preferably between about 100 mW/cm$^2$ to about 500 mW/cm$^2$, will typically be used to attain the selected power densities at the subdermal target tissue. Higher average power densities can be used in accordance with embodiments described herein. To achieve such surface power densities, the light source is preferably capable of emitting light energy having a total power output of at least about 25 mW to about 100 W. Light sources with higher total power outputs can be used in accordance with embodiments described herein. In various embodiments, the total power output is limited to be no more than about 30, 50, 75, 100, 150, 200, 250, 300, 400, or 500 mW, respectively. Higher total power outputs can be used in accordance with embodiments described herein. In addition, the light sources of certain embodiments are operated in continuous-wave (CW) mode, while in other embodiments, the light sources are pulsed with peak power outputs.

In certain embodiments, the light source comprises a plurality of sources used in combination to provide the total power output. The actual power output of the light source is preferably controllably variable. In this way, the power of the light energy emitted can be adjusted in accordance with a selected average power density at the subdermal tissue being treated.

Certain embodiments utilize a light source that includes only a single laser diode that is capable of providing about 25 mW to about 100 W of total power output. In certain such embodiments, the laser diode can be optically coupled to the patient via an optical fiber or can be configured to provide a sufficiently large spot size to avoid power densities which would burn or otherwise damage the intervening tissue. In other embodiments, the light source utilizes a plurality of sources (e.g., laser diodes) arranged in a grid or array that together are capable of providing at least about 25 mW to about 2000 W of total power output. The light source of other embodiments may also comprise sources having power capacities outside of these limits.

In certain embodiments, the efficacious period of time over which the tissue is being irradiated by the efficacious power density of light is approximately one second, and up to approximately one hour. In various embodiments, the efficacious period of time is at least about 1, 3, 5, 10, 15, 20, 30, 45, 60, 120, 180, 300, 600, 900, 1200, or 3600 seconds, depending on the desired clinical performance. In certain embodiments, the cardiac tissue is irradiated for a time period of preferably about 1 second to about 5 minutes, more preferably about 1 second to about 3 minutes, and most preferably about 3 seconds to about 3 minutes. Other period of time for irradiation are compatible with embodiments described herein. In certain embodiments, the efficacious power density and the efficacious period of time are selected to achieve an efficacious energy density at the target tissue site being treated. In certain such embodiments, the efficacious energy density is in a range between approximately 0.01 mJ/cm$^2$ and approximately 27,000 mJ/cm$^2$.

Other parameters can also be varied in the use of phototherapy in accordance with embodiments described herein. These other parameters can contribute to the light energy that is actually delivered to the treated tissue and may play key roles in the efficacy of phototherapy. Certain embodiments include irradiating a selected portion of the heart, while other embodiments irradiate the entire heart. Certain embodiments irradiate the selected portion of the heart or the entire heart by multiple irradiations of selected small portions of the heart in series.

Positioning the Light Source: Outside the Patient's Torso

The phototherapy methods for the treatment of the heart described herein may be practiced and described using, for example, a laser therapy apparatus such as that shown and described in U.S. Pat. Nos. 6,214,035, 6,267,780, 6,273,905 and 6,290,714, which are all incorporated in their entirety by reference herein, as are the references incorporated by reference therein.

FIGS. 2A-2B schematically illustrate an embodiment of a therapy apparatus 200 comprising a light source 210 configured to be placed outside the patient's torso 220. In such embodiments, positioning the light source 210 in the operational block 120 comprises placing the light source 210 outside the patient's torso 220 and interposing an element 230 between the light source 210 and the torso 220. The element 230 inhibits temperature increases at the torso 220 for an efficacious power density at the cardiac tissue being irradiated. In certain embodiments, the element 230 is part of the therapy apparatus 200, while in other embodiments, the element 230 is separate from the therapy apparatus 200.

In certain embodiments, positioning the therapy apparatus 200 on the patient's chest provides access to irradiate selected anterior portions of the heart. In other embodiments, irradiation access to selected posterior portions of the heart is provided by placing the therapy apparatus 200 on the patient's back. Other positions of the therapy apparatus 200 can be used to provide irradiation access to other selected portions of the heart.

In the embodiment illustrated by FIG. 2A, the therapy apparatus 200 comprises a light source 210 having an output emission area 211 positioned to irradiate a portion of the heart 222 with an efficacious power density and wavelength of light through intervening tissue 224. The therapy apparatus 200 further comprises an element 230 interposed between the light source 210 and the intervening tissue 224. The element 230 is configured to inhibit temperature increases at the intervening tissue 224 caused by the light.

As used herein, the term "element" is used in its broadest sense, including, but not limited to, as a reference to a constituent or distinct part of a composite device. In certain embodiments, the element 230 is configured to contact at least a portion of the patient's torso 220, as schematically illustrated in FIGS. 2A and 2B. In certain such embodiments, the element 230 is in thermal communication with and covers at least a portion of the torso 220. In other embodiments, the element 230 is spaced away from the torso 220 and does not contact the torso 220.

In certain embodiments, the light passes through the element 230 prior to reaching the torso 220 such that the element 230 is in the optical path of light propagating from the light source 210, through the skin 221, and through the bones, tissues, organs, arteries, veins, and fluids of the torso 220 (schematically illustrated in FIG. 2B by the region 223) to the heart 222. In certain embodiments, the light passes through a transmissive medium of the element 230, while in other embodiments, the light passes through an aperture of the element 230. As described more fully below, the element 230 may be utilized with various embodiments of the therapy apparatus 200.

In certain embodiments, the light source 210 is disposed on the interior surface of a housing 240 which fits securely onto the patient's torso 220. The housing 240 provides structural integrity for the therapy apparatus 200 and holds the light source 210 and element 230 in place. Exemplary materials for the housing 240 include, but are not limited to, metal, plastic, or other materials with appropriate structural integrity. The housing 240 may include an inner lining 242 comprising a stretchable fabric or mesh material, such as Lycra or nylon. The inner lining 242 is configured to contact the torso 220 while remaining outside the propagation path of the light from the light source 210 to the heart 222. In certain embodiments, the light source 210 is configured to be removably attached to the housing 240 in a plurality of positions so that the output emission area 211 of the light source 210 can be advantageously placed in a selected position for treatment of a selected portion of the heart 222. In other embodiments, the light source 210 can be an integral portion of the housing 240.

The light source 210 illustrated by FIG. 2A comprises at least one power conduit 212 coupled to a power source (not shown). In some embodiments, the power conduit 212 comprises an electrical conduit which is configured to transmit electrical signals and power to an emitter (e.g., laser diode or light-emitting diode). In certain embodiments, the power conduit 212 comprises an optical conduit (e.g., optical waveguide) which transmits optical signals and power to the output emission area 211 of the light source 210. In certain such embodiments, the light source 210 comprises optical elements (e.g., lenses, diffusers, and/or waveguides) which transmit at least a portion of the optical power received via the optical conduit 212. In still other embodiments, the therapy apparatus 200 contains a power source (e.g., a battery) and the power conduit 212 is substantially internal to the therapy apparatus 200.

In certain embodiments, the patient's torso 220 comprises hair and skin which cover the patient's chest. In other embodiments, at least a portion of the hair is removed prior to the phototherapy treatment, so that the therapy apparatus 200 substantially contacts the skin of the torso 220.

In certain embodiments, the element 230 is configured to contact the patient's torso 220, thereby providing an interface between the therapy apparatus 200 and the patient's torso 220. In certain such embodiments, the element 230 is coupled to the light source 210 and in other such embodiments, the element 230 is also configured to conform to the contours of the torso 220. In this way, the element 230 positions the output emission area 211 of the light source 210 relative to the torso 220. In certain such embodiments, the element 230 is mechanically adjustable so as to adjust the position of the light source 210 relative to the torso 220. By fitting to the torso 220 and holding the light source 210 in place, the element 230 inhibits temperature increases at the torso 220 that would otherwise result from misplacement of the light source 210 relative to the torso 220. In addition, in certain embodiments, the element 230 is mechanically adjustable so as to fit the therapy apparatus 200 to the patient's torso 220.

In certain embodiments, the element 230 provides a reusable interface between the therapy apparatus 200 and the patient's torso 220. In such embodiments, the element 230 can be cleaned or sterilized between uses of the therapy apparatus 200, particularly between uses by different patients. In other embodiments, the element 230 provides a disposable and replaceable interface between the therapy apparatus 200 and the patient's torso 220. By using pre-sterilized and pre-packaged replaceable interfaces, certain embodiments can advantageously provide sterilized interfaces without undergoing cleaning or sterilization processing immediately before use.

In certain embodiments, the element 230 comprises a container (e.g., a cavity or bag) containing a material (e.g., gel). The container can be flexible and configured to conform to the contours of the torso 220. Other exemplary materials contained in the container of the element 230 include, but are not limited to, thermal exchange materials such as glycerol and water. The element 230 of certain embodiments substantially covers a localized portion of the torso 220 in proximity to the irradiated portion of the torso 220.

In certain embodiments, at least a portion of the element 230 is within an optical path of the light from the light source 210 to the torso 220. In such embodiments, the element 230 is substantially optically transmissive at a wavelength of the light emitted by the output emission area 211 of the light source 210 and is configured to reduce back reflections of the light. By reducing back reflections, the element 230 increases the amount of light transmitted to the heart 222 and reduces the need to use a higher power light source 210 which may otherwise create temperature increases at the torso 220. In certain such embodiments, the element 230 comprises one or more optical coatings, films, layers, membranes, etc. in the optical path of the transmitted light which are configured to reduce back reflections.

In certain such embodiments, the element 230 reduces back reflections by fitting to the torso 220 so as to substantially reduce air gaps between the torso 220 and the element 230 in the optical path of the light. The refractive-index mismatches between such an air gap and the element 230 and/or the torso 220 would otherwise result in at least a portion of the light propagating from the light source 210 to the heart 222 to be reflected back towards the light source 210.

In addition, certain embodiments of the element 230 comprise a material having, at a wavelength of light emitted by the light source 210, a refractive index which substantially matches the refractive index of the torso 220 (e.g., about 1.3), thereby reducing any index-mismatch-generated back reflections between the element 230 and the torso 220. Examples of materials with refractive indices compatible with embodiments described herein include, but are not limited to, glycerol, water, and silica gels. Exemplary index-matching gels include, but are not limited to, gels available from Nye Lubricants, Inc. of Fairhaven, Mass. and "Scan Ultrasound Gel," Ref. 11-08, from Parker Laboratories, Inc. of Fairfield, N.J.

In certain embodiments, the element 230 is configured to cool the torso 220 by removing heat from the torso 220 so as to inhibit temperature increases at the torso 220. In certain such embodiments, the element 230 comprises a reservoir (e.g., a chamber or a conduit) configured to contain a coolant. The coolant flows through the reservoir near the torso 220. The torso 220 heats the coolant, which flows away from the torso 220, thereby removing heat from the torso 220 by active cooling. The coolant in certain embodiments circulates between the element 230 and a heat transfer device, such as a chiller, whereby the coolant is heated by the torso 220 and is cooled by the heat transfer device. Exemplary materials for the coolant include, but are not limited to, water or air.

In certain embodiments, the element 230 comprises a container 231 (e.g., a flexible bag) coupled to an inlet conduit 232 and an outlet conduit 233, as schematically illustrated in FIG. 3. A flowing material (e.g., water, air, or glycerol) can flow into the container 231 from the inlet conduit 232, absorb heat from the torso 220, and flow out of the container 231 through the outlet conduit 233. Certain such embodiments can provide a mechanical fit of the container 231 to the torso 220 and sufficient thermal coupling to prevent excessive heating of the torso 220 by the light. In certain embodiments, the container 231 can be disposable and replacement containers 231 can be used for subsequent patients.

In still other embodiments, the element 230 comprises a container (e.g., a flexible bag) containing a non-flowing material which does not flow out of the container but is thermally coupled to the torso 220 so as to remove heat from the torso 220 by passive cooling. Exemplary materials include, but are not limited to, water, glycerol, and gel. In certain such embodiments, the non-flowing material can be pre-cooled (e.g., by placement in a refrigerator) prior to the phototherapy treatment to facilitate cooling of the torso 220.

In certain embodiments, the element 230 is configured to apply pressure to at least a portion of the skin 221 of the torso 220 in the optical path of the light. By applying sufficient pressure, the element 230 can blanch the portion of the skin 221 by forcing at least some blood out the optical path of the light. The blood removal resulting from the pressure applied by the element 230 to the skin 221 decreases the corresponding absorption of the light by blood in the skin 221 of the torso 220. As a result, temperature increases due to absorption of the light by blood at the skin 221 of the torso 220 are reduced. As a further result, in certain embodiments, the fraction of the light transmitted to the subdermal target tissue of the heart 222 is increased.

Figure 4A:
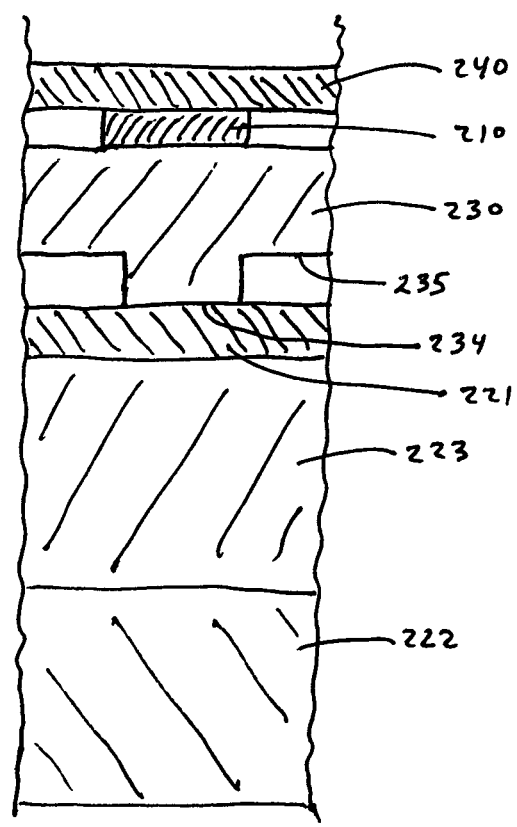
FIGS. 4A and 4B schematically illustrate embodiments of a therapy apparatus with an element with a portion spaced away from the torso and a portion contacting the skin of the torso and configured to facilitate the blanching of the skin of the torso.
Figure 4B:
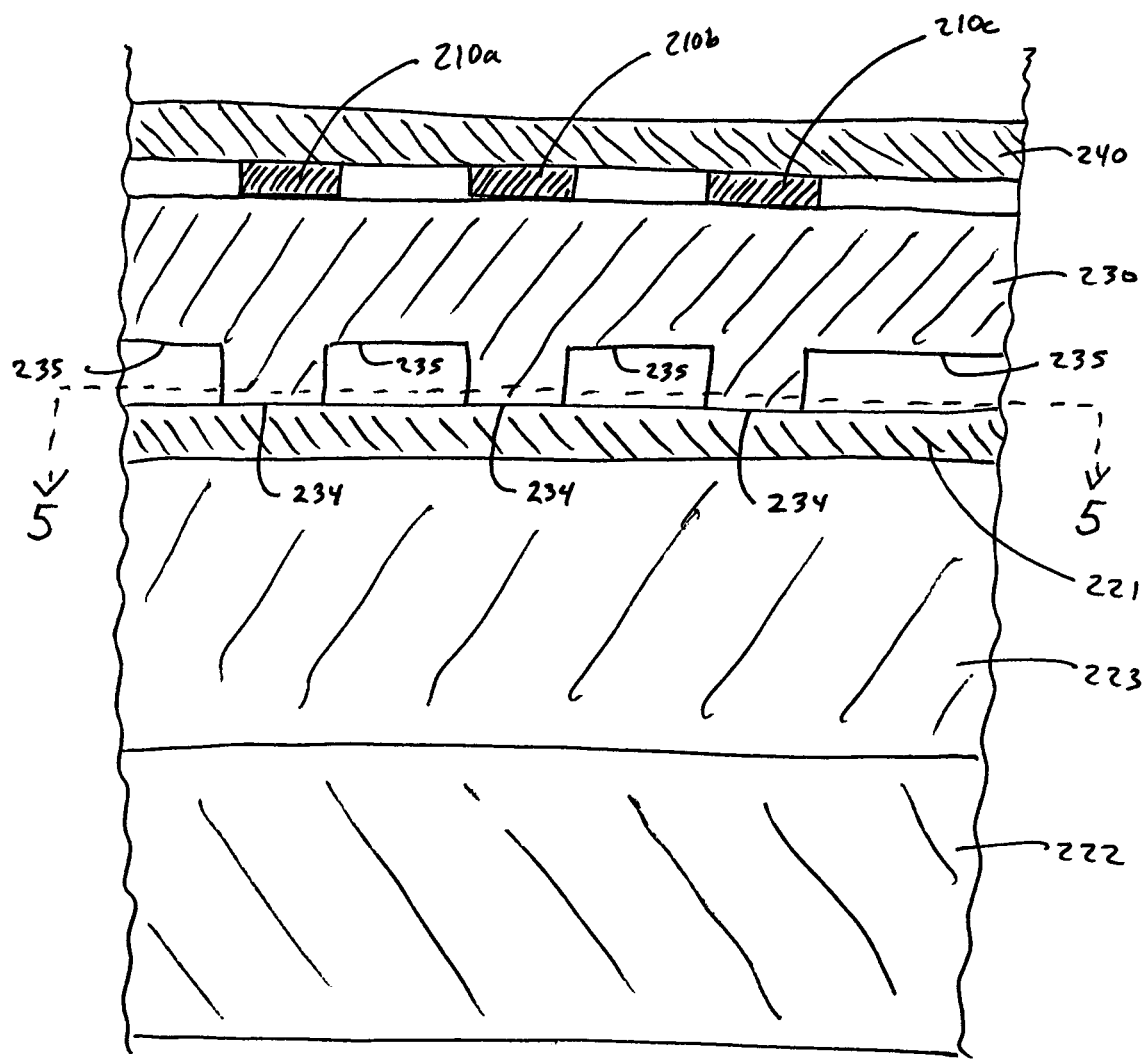

FIGS. 4A and 4B schematically illustrate embodiments of the element 230 configured to facilitate the blanching of the skin 221 of the torso 220. In the cross-sectional view of a portion of the therapy apparatus 200 schematically illustrated in FIG. 4A, certain element portions 234 contact the skin 221 and other element portions 235 are spaced away from the skin 221. The element portions 234 contacting the skin 221 provide an optical path for light to propagate from the light source 210 to the torso 220. The element portions 234 contacting the skin 221 also apply pressure to the skin 221, thereby forcing blood out from beneath the element portion 234. FIG. 4B schematically illustrates a similar view of an embodiment in which the light source 210 comprises a plurality of light sources 210a, 210b, 210c.

Figure 5A:
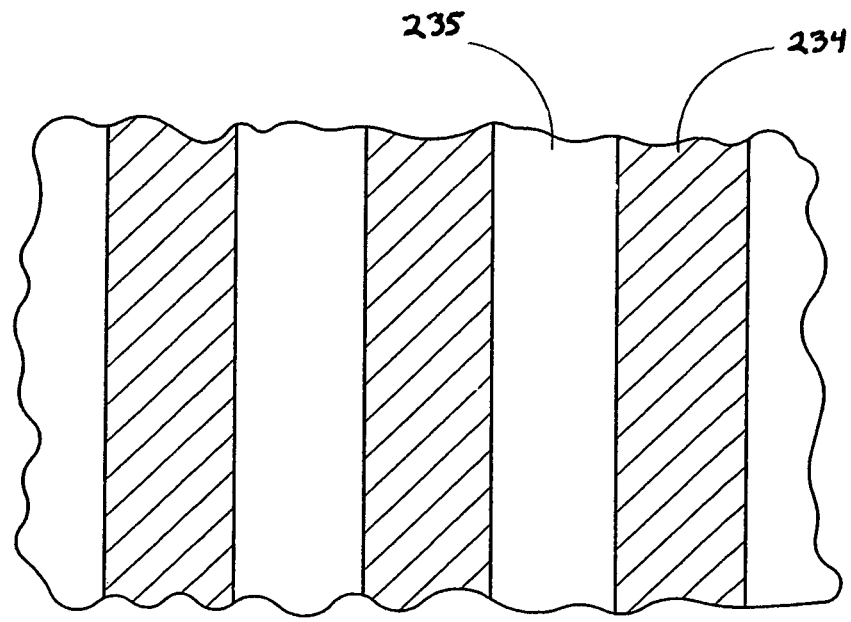
FIGS. 5A and 5B schematically illustrate cross-sectional views of two embodiments of the element in accordance with FIG. 4B taken along the line 5-5.
Figure 5B:
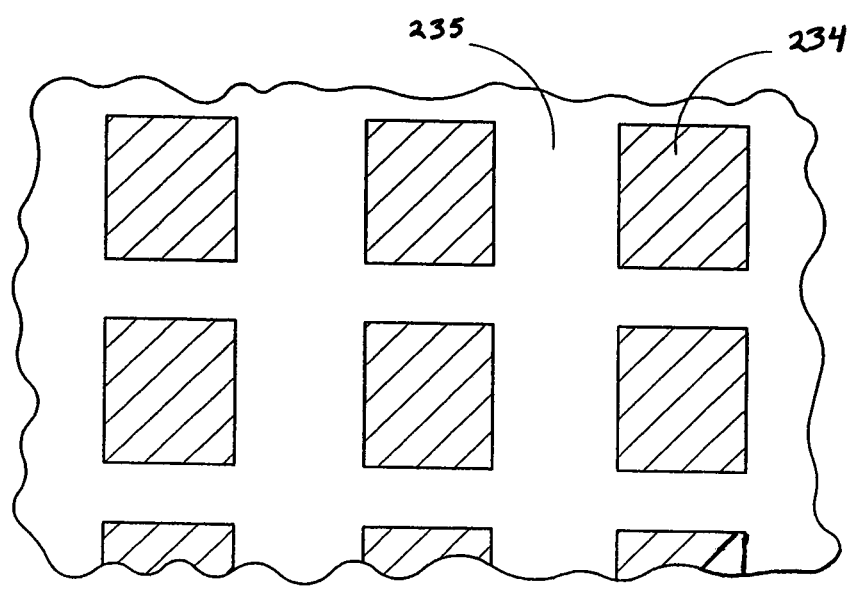

FIG. 5A schematically illustrates one embodiment of the cross-section along the line 5-5 of FIG. 4B. The element portions 234 contacting the skin 221 comprise ridges extending along one direction, and the element portions 235 spaced away from the skin 221 comprise troughs extending along the same direction. In certain embodiments, the ridges are substantially parallel to one another and the troughs are substantially parallel to one another. FIG. 5B schematically illustrates another embodiment of the cross-section along the line 5-5 of FIG. 4B. The element portions 234 contacting the skin 221 comprise a plurality of projections in the form of a grid or array. More specifically, the portions 234 are rectangular and are separated by element portions 235 spaced away from the skin 221, which form troughs extending in two substantially perpendicular directions. The portions 234 of the element 230 contacting the skin 221 can be a substantial fraction of the total area of the element 230.

Figure 6A:
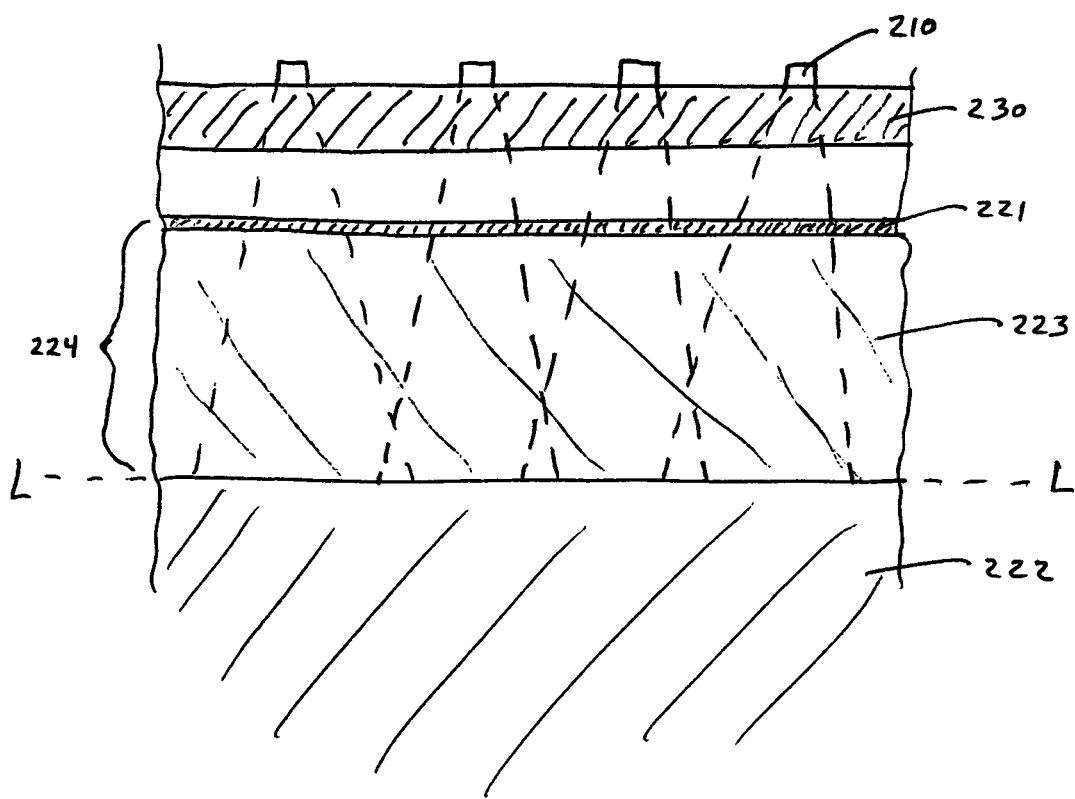
FIGS. 6A-6C schematically illustrate an embodiment in which light emitted by the light sources propagates from the light sources through the intervening tissue, including the skin of the torso, to the heart and disperses in a direction generally parallel to the skin.
Figure 6B:
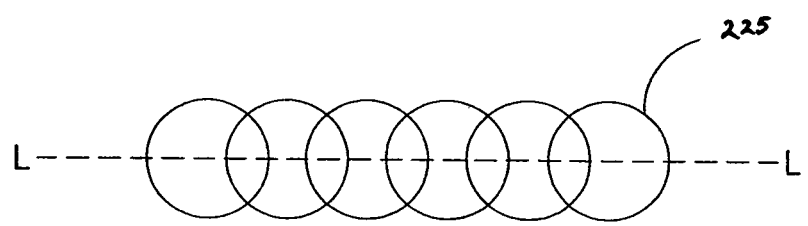
Figure 6C:
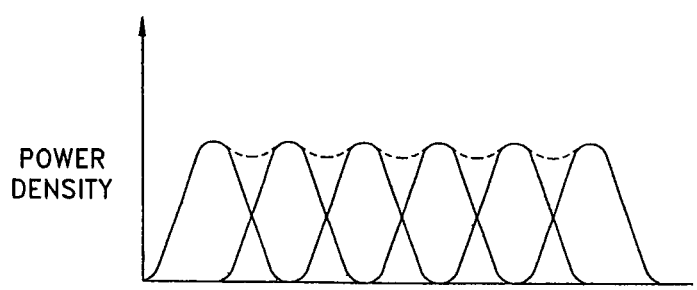

FIGS. 6A-6C schematically illustrate an embodiment in which light emitted by the light sources 210 propagates from the light sources 210 through the intervening tissue 224, including the skin 221, of the torso 220 to the heart 222 and disperses in a direction generally parallel to the skin 221, as shown in FIG. 6A. While FIG. 6A shows the light sources 210 and the element 230 spaced away from the torso 220, in other embodiments, the element 230 contacts the torso 220. The light sources 210 are preferably spaced sufficiently far apart from one another such that the light emitted from each light source 210 overlaps with the light emitted from the neighboring light sources 210 at the heart 222. FIG. 6B schematically illustrates this overlap as the overlap of circular spots 225 at a reference depth at or below the surface of the heart 222. FIG. 6C schematically illustrates this overlap as a graph of the power density at the reference depth of the heart 222 along the line L-L of FIGS. 6A and 6B. Summing the power densities from the neighboring light sources 210 (shown as a dashed line in FIG. 6C) serves to provide a more uniform light distribution at the tissue to be treated. In such embodiments, the summed power density is preferably less than a damage threshold of the heart 222 and above an efficacy threshold.

Figure 7A:
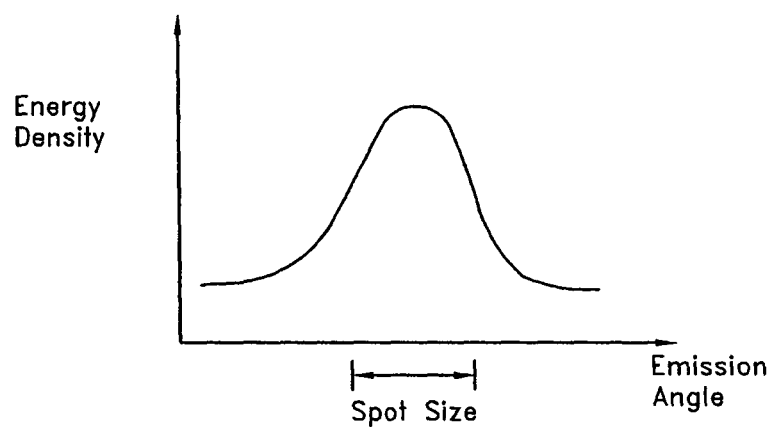
FIGS. 7A and 7B schematically illustrate the diffusive effect on the light by the element.
Figure 7B:
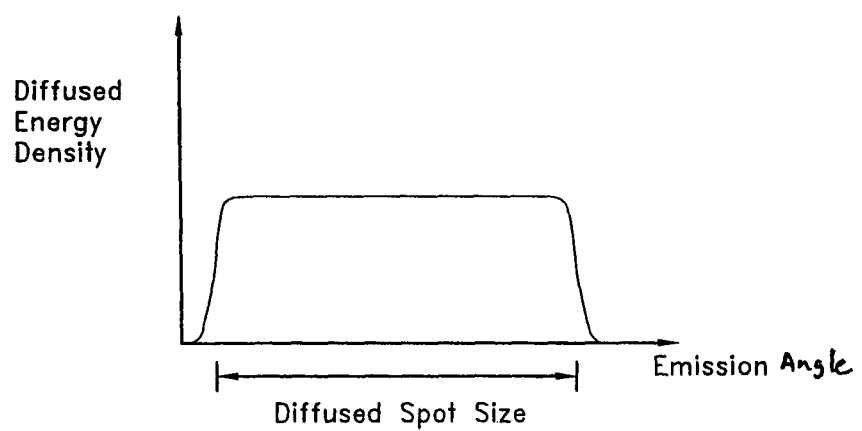

In certain embodiments, the element 230 is configured to diffuse the light prior to reaching the torso 220. FIGS. 7A and 7B schematically illustrate the diffusive effect on the light by the element 230. An exemplary energy density profile of the light emitted by a light source 210, as illustrated by FIG. 7A, is peaked at a particular emission angle. After being diffused by the element 230, as illustrated by FIG. 7B, the energy density profile of the light does not have a substantial peak at any particular emission angle, but is substantially evenly distributed among a range of emission angles. By diffusing the light emitted by the light source 210, the element 230 distributes the light energy substantially evenly over the area to be illuminated, thereby inhibiting "hot spots" which would otherwise create temperature increases at the torso 220. In addition, by diffusing the light prior to its reaching the torso 220, the element 230 can effectively increase the spot size of the light impinging the skin 221 of the torso 220, thereby advantageously lowering the power density at the torso 220, as described more fully below. In addition, in embodiments with multiple light sources 210, the element 230 can diffuse the light to alter the total light output distribution to reduce inhomogeneities.

In certain embodiments, the element 230 provides sufficient diffusion of the light such that the power density of the light is less than a maximum tolerable level of the torso 220 and heart 222. In certain other embodiments, the element 230 provides sufficient diffusion of the light such that the power density of the light equals a therapeutic value at the target tissue. The element 230 can comprise exemplary diffusers including, but are not limited to, holographic diffusers such as those available from Physical Optics Corp. of Torrance, Calif. and Display Optics P/N SN1333 from Reflexite Corp. of Avon, Conn.

In certain embodiments in which a plurality of light sources 210 are used, the light sources 210 are selectively activated individually or in groups to provide predetermined irradiation patterns on the torso 220. These irradiation patterns can comprise irradiated areas and non-irradiated areas, which in certain embodiments, are varied as functions of time. In addition, the light sources 210 can be pulsed in selected groups or all together. This selective irradiation can be used to reduce the thermal load on particular locations of the torso 220 by limiting the amount of irradiation to any one particular area of the torso 220. Thus, the thermal load at the torso 220 due to the absorption of the light can be distributed across the torso 220, thereby avoiding unduly heating one or more portions of the torso 220. In certain embodiments, the irradiated area is a substantial fraction of the total area of the heart, and in other embodiments, the irradiated area includes the total area of the heart. As described more fully below, in certain embodiments, the selective irradiation can be used to reduce the amount of scattering and absorption of the light by the lungs during the treatment procedure.

Figure 8A:
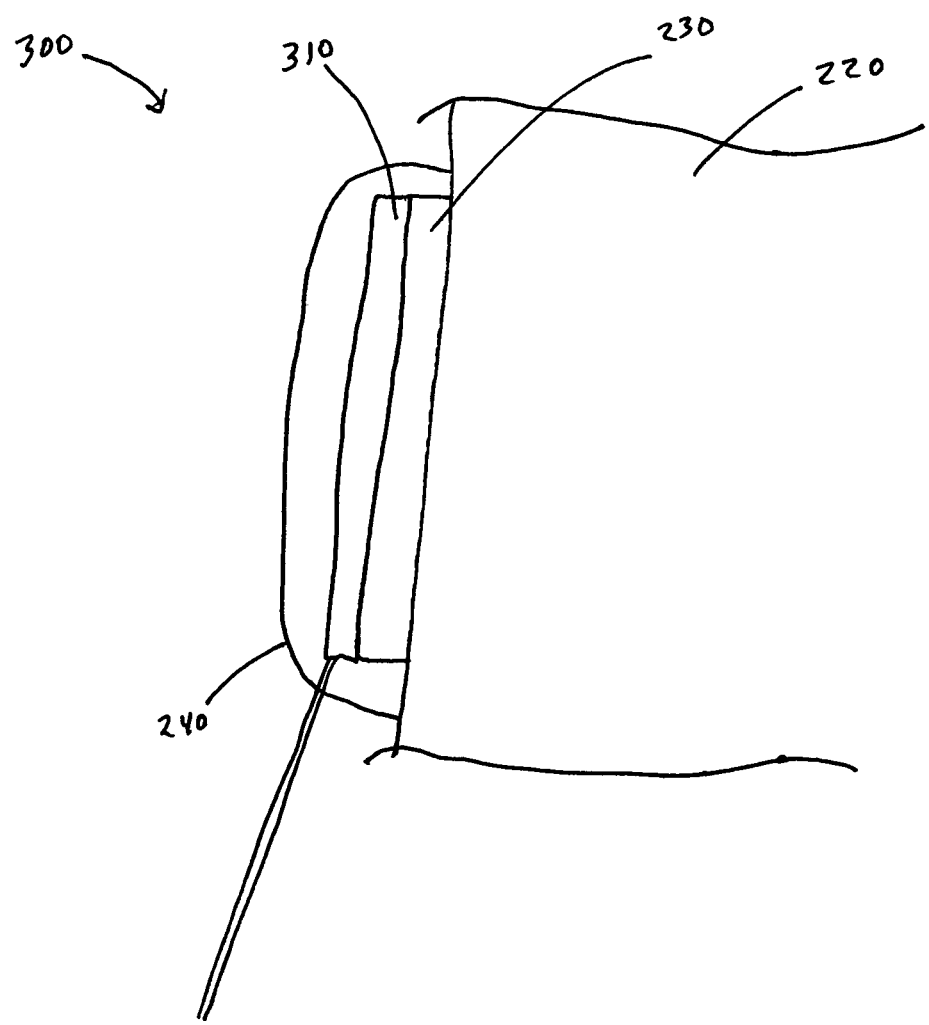
FIGS. 8A-8C schematically illustrate embodiments of the therapy apparatus with a light source comprising a light-emitting blanket.
Figure 8B:
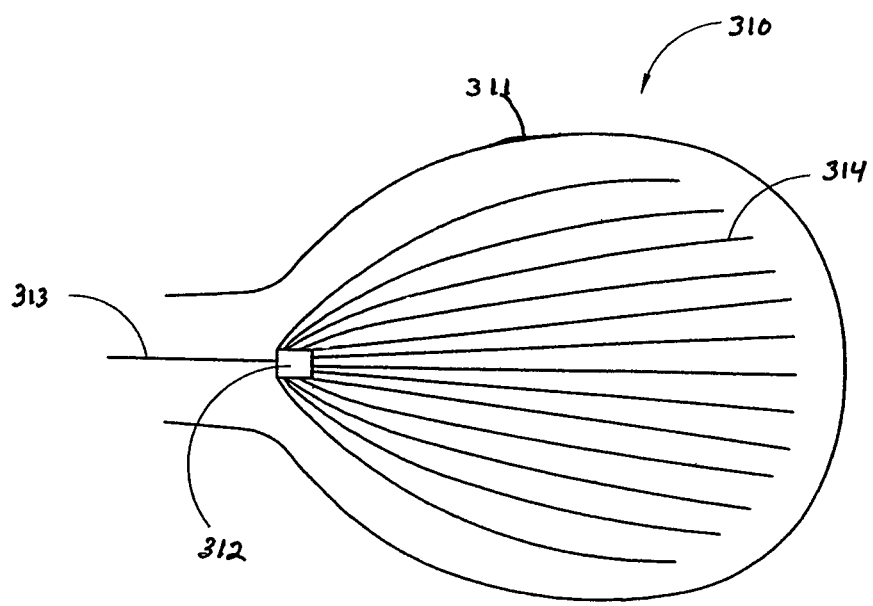
Figure 8C:
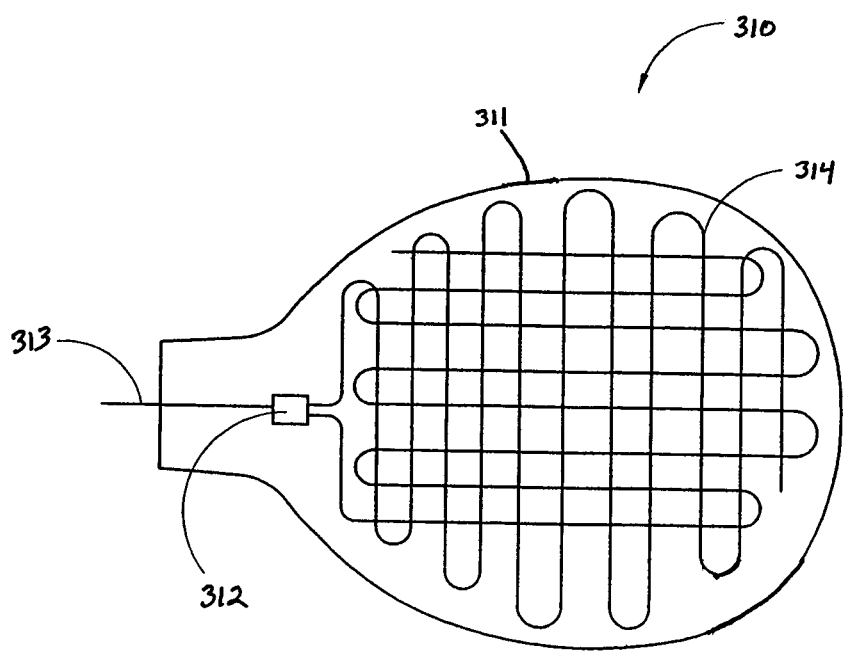

FIG. 8A schematically illustrates another embodiment of the therapy apparatus 300 which comprises the housing 240 and a light source comprising a light-emitting blanket 310. FIG. 8B schematically illustrates an embodiment of the blanket 310 comprising a flexible substrate 311 (e.g., flexible circuit board), a power conduit interface 312, and a sheet formed by optical fibers 314 positioned in a fan-like configuration. FIG. 8C schematically illustrates an embodiment of the blanket 310 comprising a flexible substrate 311, a power conduit interface 312, and a sheet formed by a plurality of optical fibers 314 woven into a mesh. The blanket 310 is preferably positioned within the housing 240 so as to cover an area of the torso 220 corresponding to a portion of the heart 222 to be treated.

In certain such embodiments, the power conduit interface 312 is configured to be coupled to an optical fiber conduit 313 which provides optical power to the blanket 310. The optical power interface 312 of certain embodiments comprises a beam splitter or other optical device which distributes the incoming optical power among the various optical fibers 314. In other embodiments, the power conduit interface 312 is configured to be coupled to an electrical conduit which provides electrical power to the blanket 310. In certain such embodiments, the power conduit interface 312 comprises one or more laser diodes, the output of which is distributed among the various optical fibers 314 of the blanket 310.

In certain other embodiments, the blanket 310 comprises an electroluminescent sheet which responds to electrical signals from the power conduit interface 312 by emitting light. In such embodiments, the power conduit interface 312 comprises circuitry configured to distribute the electrical signals to appropriate portions of the electroluminescent sheet.

The side of the blanket 310 nearer the torso 220 is preferably provided with a light scattering surface, such as a roughened surface to increase the amount of light scattered out of the blanket 310 towards the torso 220. The side of the blanket 310 further from the torso 220 is preferably covered by a reflective coating so that light emitted away from the torso 220 is reflected back towards the torso 220. This configuration is similar to configurations used for the "back illumination" of liquid-crystal displays (LCDs). Other configurations of the blanket 310 are compatible with embodiments described herein.

In certain embodiments, the light source 210 generates light which cause eye damage if viewed by an individual. In such embodiments, the apparatus 200 can be configured to provide eye protection so as to avoid viewing of the light by individuals. For example, opaque materials can be appropriately placed to block the light from being viewed directly. In addition, interlocks can be provided so that the light source 210 is not activated unless the apparatus 200 is in place, or other appropriate safety measures are taken.

Figure 9:
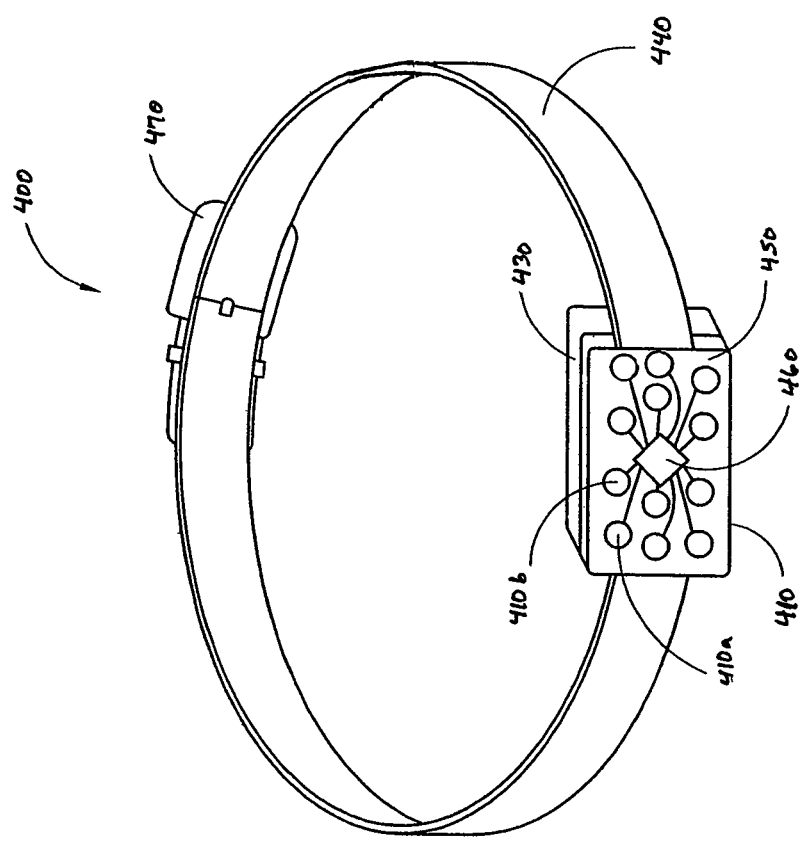
FIG. 9 schematically illustrates an embodiment of the therapy apparatus with a light source, an element, and a flexible strap configured for securing the therapy apparatus over an area of the patient's torso.

Another suitable phototherapy apparatus in accordance with embodiments described here is illustrated in FIG. 9. The illustrated therapy apparatus 400 includes a light source 410, an element 430, and a flexible strap 440 configured for securing the therapy apparatus 400 over an area of the patient's torso. The light source 410 can be disposed on the strap 440 itself, or in a housing 450 coupled to the strap 440. The light source 410 preferably comprises a plurality of diodes 410a, 410b, . . . capable of emitting light energy having a wavelength in the visible to near-infrared wavelength range. The element 430 is configured to be positioned between the light source 410 and the patient's torso 220.

The therapy apparatus 400 further includes a power supply (not shown) operatively coupled to the light source 410, and a programmable controller 460 operatively coupled to the light source 410 and to the power supply. The programmable controller 460 is configured to control the light source 410 so as to deliver a predetermined power density to the target cardiac tissue. In certain embodiments, as schematically illustrated in FIG. 9, the light source 410 comprises the programmable controller 460. In other embodiments the programmable controller 460 is a separate component of the therapy apparatus 400.

In certain embodiments, the strap 440 comprises a loop of elastomeric material sized appropriately to fit snugly onto the patient's torso 220. In other embodiments, the strap 440 comprises an elastomeric material to which is secured any suitable securing means 470, such as mating Velcro strips, buckles, snaps, hooks, buttons, ties, or the like. The precise configuration of the strap 440 is subject only to the limitation that the strap 440 is capable of maintaining the light source 410 in a selected position so that light energy emitted by the light source 410 is directed towards the targeted cardiac tissue.

In the exemplary embodiment illustrated in FIG. 9, the housing 450 comprises a layer of flexible plastic or fabric that is secured to the strap 440. In other embodiments, the housing 450 comprises a plate or an enlarged portion of the strap 440. Various strap configurations and spatial distributions of the light sources 410 are compatible with embodiments described herein so that the therapy apparatus 400 can treat selected portions of cardiac tissue.

Figure 10:
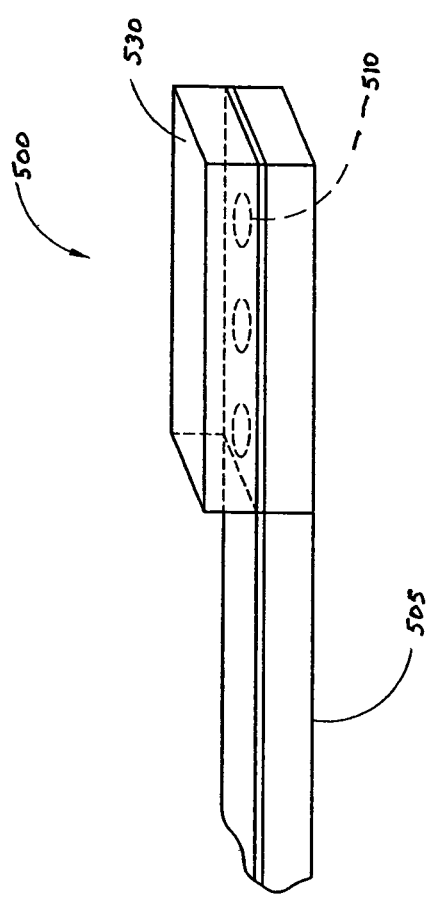
FIG. 10 schematically illustrates an embodiment of the therapy apparatus with a handheld probe.

In still other embodiments, a therapy apparatus 500 for delivering the light energy includes a handheld probe 505, as schematically illustrated in FIG. 10. The probe 505 includes a light source 510 and an element 530 as described herein.

Positioning the Light Source: Within the Torso

Figure 11A:
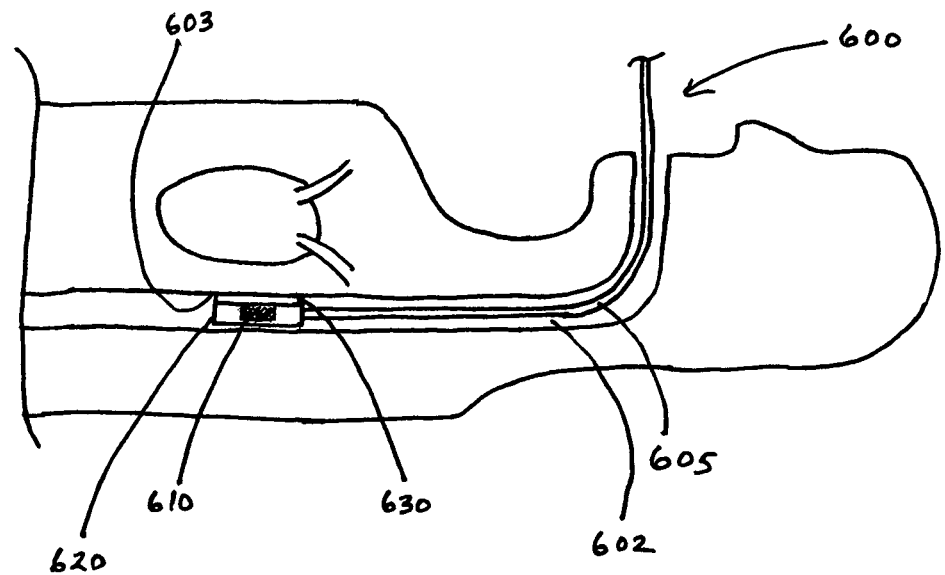
FIGS. 11A and 11B schematically illustrate embodiments of a therapy apparatus configured to be inserted into the esophagus of the patient.
Figure 11B:
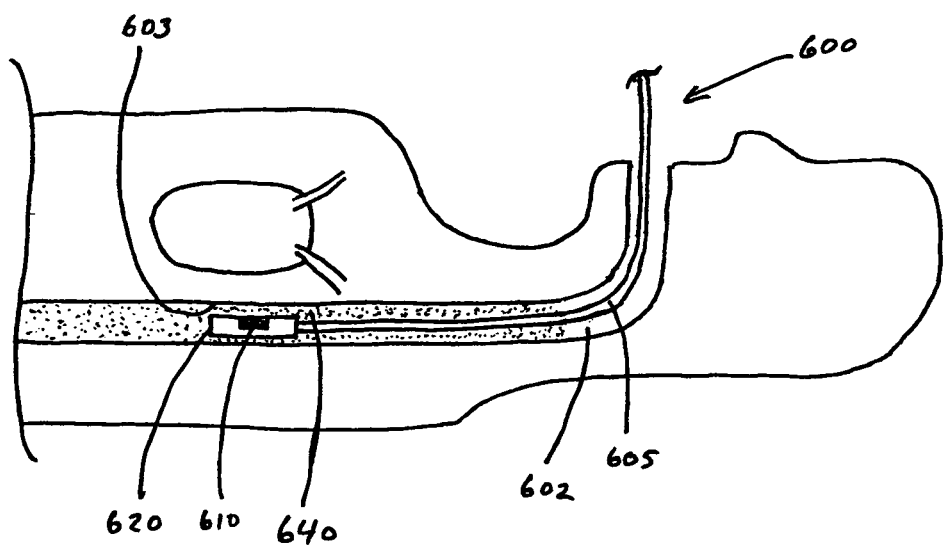

FIGS. 1A and 11B schematically illustrate embodiments of a therapy apparatus 600 configured to be inserted into the esophagus 602 of the patient. The therapy apparatus 600 comprises a flexible probe 605 and a light source 610 located on a distal end 620 of the probe 605. In certain embodiments, as illustrated by FIG. 11A, the distal end 620 of the probe 605 is configured to contact a surface 603 of the esophagus 602. In certain such embodiments, the distal end 620 of the probe 605 further comprises an element 630 interposed between the light source 610 and the surface 603 of the esophagus 602. As described above in relation to embodiments positioned outside the torso, the element 630 is configured to inhibit temperature increases at the esophagus 602 for an efficacious power density at the cardiac tissue.

In certain other embodiments, as illustrated by FIG. 11B, the esophagus 602 contains a material 640 which serves as the element 630. In certain embodiments, the material 640 (e.g., water) has a refractive index which substantially matches the refractive index of the inside surface 603 of the esophagus 602, thereby reducing any index-mismatch-generated back reflections between the distal end 620 and the esophagus 602. In addition, the material 640 can provide cooling to the esophagus 602 to inhibit temperature increases. The material 640 can also advantageously diffuse the light from the light source 610.

By inserting the therapy apparatus 600 into the esophagus 602, the therapy apparatus 600 can treat portions of the heart which are not accessible by other embodiments described herein. For example, upon insertion into the esophagus 602, the light source 610 of the therapy apparatus 600 is closer to the cardiac tissue to be irradiated than in embodiments with a light source positioned outside the torso. Thus, the therapy apparatus 600 can provide phototherapy using lower initial power densities since there is less intervening tissue to absorb or scatter the light. In addition, such embodiments can more easily irradiate selected posterior portions of the heart.

FIG. 12 schematically illustrates an embodiment of a therapy apparatus 700 configured to be inserted into a blood vessel 702 of the patient. The therapy apparatus 700 comprises a catheter 705 and a light source 710 located on a distal end 720 of the catheter 705. In certain embodiments, the catheter 705 is introduced into either an artery or a vein and positioned so that the light source 710 is in proximity to cardiac tissue. The catheter 705 is introduced interfemorally in certain embodiments by inserting the catheter 705 into a femoral artery. The catheter 705 is introduced interclavicularly in certain other embodiments by inserting the catheter 705 into a clavicular artery. By placing the light source 710 in proximity to the cardiac tissue to be irradiated, such embodiments avoid having the light absorbed or scattered by intervening tissue such as the lungs. An exemplary catheter is described by U.S. Pat. No. 6,443,974 issued to Oron et al., which is incorporated in its entirety by reference herein.

FIG. 13A schematically illustrates an embodiment of a therapy apparatus 800 configured to avoid a portion of intervening tissue between the therapy apparatus 800 and the heart 222. The therapy apparatus 800 comprises at least one light source 810 which comprises at least one needle 820. In certain embodiments, the needle 820 comprises an optical fiber 822 that has a first end 823 optically coupled to the light source 810, as illustrated in FIG. 13A. The needle 820 is positioned so that a second end 824 of the optical fiber 822 is inserted into the torso 220. By transmitting light from the light source 810 into the torso 220, such embodiments avoid scattering or absorption by a portion of the intervening tissue of the torso 220.

In certain embodiments, the needle 820 is inserted through at least a portion of the skin of the patient's torso 220. In certain such embodiments, the second end 824 of the optical fiber 822 is past the skin 221 of the torso 220, thereby avoiding scattering or absorption by the skin 221 of light transmitted to the heart 222. In other embodiments, the second end 824 is inserted deeper into the torso 220, past portions of bone, muscles, and other tissue, so that these tissues do not scatter or absorb the light transmitted from the therapy apparatus 800 to the heart 222. In still other embodiments, the second end 824 is inserted such that the needle 820 does not puncture the pericardium surrounding the heart 222. Other positions of the needle 820 are compatible with embodiments described herein.

FIG. 13B schematically illustrates an embodiment of the therapy apparatus 800 with a plurality of transdermal needles 820. In the embodiment illustrated by FIG. 13B, each needle 820 itself is optically transmissive at the wavelength of light from the light source 810. Thus, each needle 820 serves as a portion of an optical fiber 822 with a second end 824 inserted into the torso 220. In certain embodiments, each needle 820 comprises a lumen or other conduit through which the light from the light source 810 is transmitted into the torso 220.

Each needle 820 extends through at least a portion of the skin 221 of the torso 220. In such embodiments, the light emitted from the second end 824 of the optical fiber 822 avoids scattering or absorption by the outermost layers of the skin 221. In certain such embodiments, the needles 820 extend approximately halfway through the muscle wall of the chest to be within approximately 3 millimeters of bone. The needles 820 are preferably biocompatible and strong enough to withstand the insertion process.

Exemplary needles 820 in accordance with embodiments described herein include silicon microneedles, such as those described by U.S. Pat. No. 5,928,207 issued to Pisano et al. and U.S. Pat. No. 6,187,210 issued to Lebouitz et al., each of which is incorporated by reference herein. Other exemplary microneedles are described by Brazzle et al. in "*Active Microneedles with Integrated Functionality,*" Technical Digest of the 2000 Solid-State Sensor and Actuator Workshop, Hilton Head Isl., S.C., 06/04-08/00, Transducer Research Foundation, Cleveland (2000), pp. 199-202, which is incorporated in its entirety by reference herein.

In certain embodiments, phototherapy is performed by directly irradiating the cardiac tissue after a sufficient opening has been made in the chest. In certain such embodiments, the opening is made for a cardiac bypass surgical procedure. The phototherapy can provide a cardio-protective, healing-accelerating mechanism. The phototherapy can be performed before, during, after, or a combination thereof, the bypass surgical procedure. In other embodiments, the opening is made expressly for placing the therapy apparatus in proximity to the heart 222. In certain such embodiments, the intervening tissue is at a minimum, while in other embodiments in which the therapy apparatus contacts the target cardiac tissue, the intervening tissue is effectively nonexistent.

In still other embodiments, at least a portion of the therapy apparatus is implanted within the torso 220 in proximity to the heart 222. Such "pacemaker"-type embodiments can deliver light to a selected portion of the heart 222 while minimizing the scattering and absorption by intervening tissue. Such embodiments can implant a light source comprising a small laser or one or more battery-operated light-emitting diodes and use the light source to irradiate a selected portion of the heart.

In other embodiments, the blood can be irradiated within an artery (e.g., by placing a laser or an optical fiber within the artery). The irradiated blood then has more ATP which gets to the heart. In other embodiments, the blood can be removed from the body, irradiated outside the body, and returned to the body to carry ATP to the heart.

Directing Light Onto Cardiac Tissue: Power Density

Phototherapy for the treatment of cardiac tissue after a myocardial infarction (MI) is based in part on the discovery that power density (i.e., power per unit area or number of photons per unit area per unit time) and energy density (i.e., energy per unit area or number of photons per unit area or power density multiplied by the exposure time) of the light energy applied to tissue are significant factors in determining the relative efficacy of low level phototherapy. Contrary to previous understanding in the prior art, efficacy is not as directly related to the total power or the total energy delivered to the tissue. This discovery is particularly applicable with respect to treating and saving surviving but endangered cardiac tissue in a zone of danger surrounding the primary infarct after an MI. Preferred methods described herein are based at least in part on the finding that, given a selected wavelength of light energy, it is the power density and/or the energy density of the light delivered to cardiac tissue (as opposed to the total power or total energy delivered to the cardiac tissue) that appears to be important factors in determining the relative efficacy of phototherapy in treating patients after experiencing an MI.

Without being bound by theory, it is believed that light energy delivered within a certain range of power densities and energy densities provides the desired biostimulative effect on the intracellular environment, such that proper function is returned to previously nonfunctioning or poorly functioning mitochondria in at-risk cardiac cells. The biostimulative effect may include interactions with chromophores within the target tissue, which facilitate production of ATP thereby feeding energy to injured cells which have experienced decreased blood flow due to the MI. Because MIs correspond to blockages or other interruptions of blood flow to portions of the heart, it is thought that any effects of increasing blood flow by phototherapy are of less importance in the efficacy of phototherapy for MI victims. Further information regarding the role of power density and exposure time in phototherapy is described by Hans H.F.I. van Breugel and P. R. Dop Bär in "*Power Density and Exposure Time of He—Ne Laser Irradiation Are More Important Than Total Energy Dose in Photo-Biomodulation of Human Fibroblasts In Vitro*," Lasers in Surgery and Medicine, Volume 12, pp. 528-537 (1992), which is incorporated in its entirety by reference herein.

In embodiments described herein, an efficacious power density of light is directed onto cardiac tissue. In certain such embodiments, a cardioprotective-effective power density of light is provided to a patient that has experienced an ischemic event in the heart, thereby providing a cardioprotective effect.

As used herein, the term "cardiodegeneration" refers to the process of cardiac cell destruction resulting from primary destructive events such as MI, as well as from secondary, delayed and progressive destructive mechanisms that are invoked by cells due to the occurrence of the primary destructive event. Primary destructive events include disease processes or physical injury or insult, including MI, but also include other diseases and conditions such as physical trauma or acute injury or insult. Secondary destructive mechanisms include any mechanism that leads to the generation and release of molecules toxic to cardiac cells, including apoptosis, depletion of cellular energy stores because of changes in mitochondrial membrane permeability, release or failure in the reuptake of excessive glutamate, reperfusion injury, and activity of cytokines and inflammation. Both primary and secondary mechanisms contribute to forming a "zone of danger" for cardiac cells, wherein the cardiac cells in the zone have at least temporarily survived the primary destructive event, but are at risk of dying due to processes having delayed effect.

As used herein, the term "cardioprotection" refers to a therapeutic strategy for slowing or preventing the otherwise irreversible loss of cardiac cells due to cardiodegeneration after a primary destructive event, whether the cardiodegeneration loss is due to disease mechanisms associated with the primary destructive event or secondary destructive mechanisms.

As used herein, the term "cardioprotective-effective" refers to a characteristic of an amount of light energy. A cardioprotective-effective amount of light energy achieves the goal of preventing, avoiding, reducing, or eliminating cardiodegeneration. In certain embodiments, a cardioprotective-effective amount is a power density of the light energy measured in $mW/cm^2$, while in other embodiments, a cardioprotective-effective amount is an energy density of the light energy measured in $mJ/cm^2$.

Thus, in certain embodiments, a method of phototherapy involves delivering a cardioprotective-effective amount of light energy having a wavelength in the visible to near-infrared wavelength range to a target area of the patient's heart 222. In certain embodiments, the target area of the patient's heart 222 includes the area of infarct, i.e. to cardiac cells within the "zone of danger."

In other embodiments, the target area includes portions of the heart 222 not within the zone of danger. In certain such embodiments, irradiation of healthy cardiac cells outside the zone of danger can treat and save surviving but endangered cardiac cells in the zone of danger surrounding the infarcted area. Without being bound by theory, it is believed that irradiation of healthy tissue in proximity to the zone of danger increases the production of ATP and copper ions in the healthy tissue and which then migrate to the injured cells within the region surrounding the infarct, thereby producing beneficial effects. Additional information regarding the biomedical mechanisms or reactions involved in phototherapy is provided by Tiina I. Karu in "*Mechanisms of Low-Power Laser Light Action on Cellular Level*", Proceedings of SPIE Vol. 4159 (2000), Effects of Low-Power Light on Biological Systems V, Ed. Rachel Lubart, pp. 1-17, which is incorporated in its entirety by reference herein.

Figure 14B:
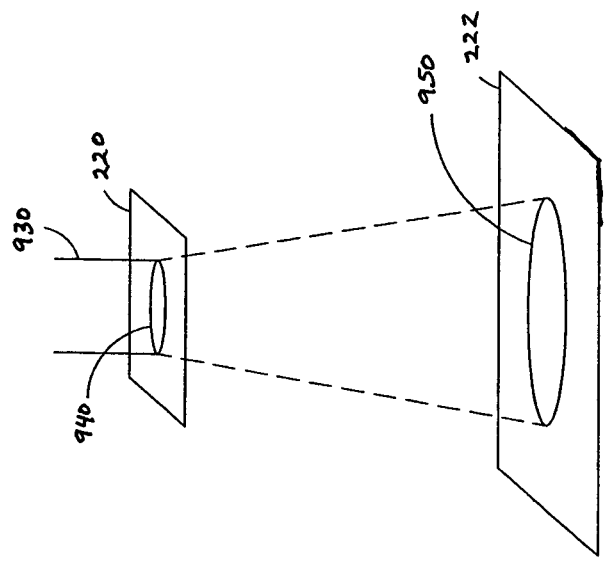
FIGS. 14A and 14B schematically illustrates two light beams having different cross-sections impinging a patient's torso and propagating through the patient's torso to irradiate a portion of the patient's heart.
Figure 14A:
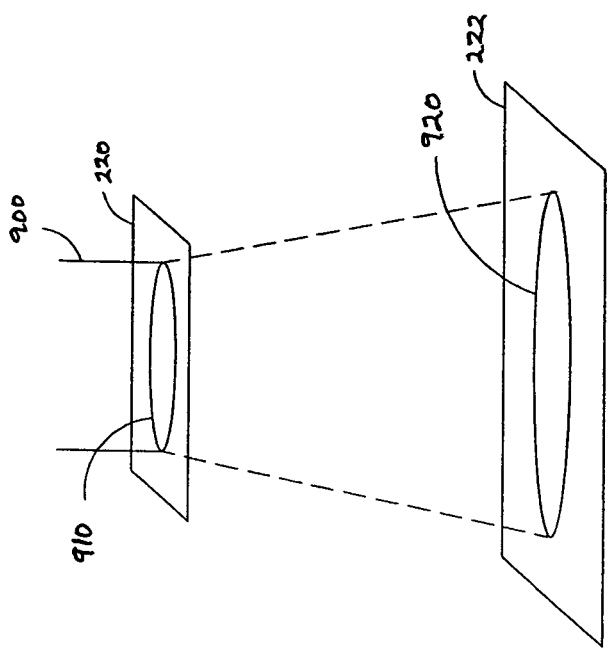

The significance of the power density used in phototherapy has ramifications with regard to the devices and methods used in phototherapy treatments of cardiac tissue, as schematically illustrated by FIGS. 14A and 14B, which show the effects of scattering by intervening tissue. Further information regarding the scattering of light by tissue is provided by V. Tuchin in "*Tissue Optics: Light Scattering Methods and Instruments for Medical Diagnosis,*" SPIE Press (2000), Bellingham, Wash., pp. 3-11, which is incorporated in its entirety by reference herein.

FIG. 14A schematically illustrates a light beam 900 impinging a portion 910 of a patient's torso 220 and propagating through the patient's torso 220 to irradiate a portion 920 of the patient's heart 222. In the exemplary embodiment of FIG. 14A, the light beam 900 impinging the torso 220 has a circular cross-section with a radius of 2 centimeters and a cross-sectional area of approximately 12.5 $cm^2$. For comparison purposes, FIG. 14B schematically illustrates a light beam 930 having a significantly smaller cross-section impinging a smaller portion 940 of the torso 220 to irradiate a portion 950 of the heart 222. The light beam 930 impinging the torso 220 in FIG. 14B has a circular cross-section with a radius of 1 centimeter and a cross-sectional area of approximately 3.1 $cm^2$. The cross-sections and radii of the light beams 900, 930 illustrated in FIGS. 14A and 14B are exemplary; other light beams with other parameters are also compatible with embodiments described herein. In particular, similar considerations apply to focussed beams, collimated beams, or diverging beams, as they are similarly scattered by the intervening tissue.

As shown in FIGS. 14A and 14B, the cross-sections of the light beams 900, 930 become larger while propagating through the torso 220 due to scattering from interactions with tissue. The light beams 900, 930 propagate through various tissue portions, each with a characteristic angle of dispersion, with the light beams 900, 930 experiencing an effective angle of dispersion. Assuming that the effective angle of dispersion is 15 degrees and the irradiated cardiac tissue of the heart 220 is 7 centimeters below the surface of the torso 220, the resulting area of the portion 920 of the heart 222 irradiated by the light beam 900 in FIG. 14A is approximately 45.6 $cm^2$. Similarly, the resulting area of the portion 950 of the heart 222 irradiated by the light beam 930 in FIG. 14B is approximately 24.8 $cm^2$.

Irradiating the portion 920 of the heart 222 with a power density of 10 $mW/cm^2$ corresponds to a total power within the portion 920 of approximately 456 mW (10 mW/cm²× 45.6 cm²). Assuming only approximately 0.5% of the light beam 900 is transmitted between the surface of the torso 220 and the heart 222, the incident light beam 900 at the surface of the torso 220 will have a total power of approximately 91200 mW (456 mW/0.005) and a power density of approximately 7300 mW/cm² (91200 mW/12.5 cm²). Similarly, irradiating the portion 950 of the heart 222 with a power density of 10 mW/cm² corresponds to a total power within the portion 950 of approximately 248 mW (10 mW/cm²× 24.8 cm²), and with the same 0.5% transmittance, the incident light beam 950 at the surface of the torso 220 will have a total power of approximately 49600 mW (248 mW/0.005) and a power density of approximately 15790 mW/cm² (49600 mW/3.1 cm²). These calculations are summarized in Table 1.

TABLE 1

|  | 2 cm Spot Size (FIG. 14A) | 1 cm Spot Size (FIG. 14B) |
| --- | --- | --- |
| Surface of Torso: | | |
| Area | 12.5 cm² | 3.1 cm² |
| Total power | 91200 mW | 49600 mW |
| Power density | 7300 mW/cm² | 15790 mW/cm² |
| Heart: | | |
| Area | 45.6 cm² | 24.8 cm² |
| Total power | 456 mW | 248 mW |
| Power density | 10 mW/cm² | 10 mW/cm² |

These exemplary calculations illustrate that to obtain a desired power density at the heart 222, higher total power at the surface of the torso 220 can be used in conjunction with a larger spot size at the surface of the torso 220. Thus, by increasing the spot size at the surface of the torso 220, a desired power density at the heart 222 can be achieved with lower power densities at the surface of the torso 220 which can reduce the possibility of overheating the torso 220. In certain embodiments, the light can be directed through an aperture to define the illumination of the torso 220 to a selected smaller area.

Directing Light Onto Cardiac Tissue: Other Parameters

In certain embodiments, delivering the cardioprotective amount of light energy includes selecting an initial power density of the light energy at the torso 220 corresponding to the predetermined efficacious power density at the target area of the heart 222. As described above, light propagating through tissue is scattered and absorbed by the tissue. Calculations of the initial power density to be applied to the torso 220 so as to deliver a predetermined efficacious power density to the selected target area of the heart 222 preferably take into account the attenuation of the light energy as it propagates through the skin and other tissues, such as bone and lung tissue. Factors known to affect the attenuation of light propagating to the heart 222 include, but are not limited to, skin pigmentation, the presence and color of hair over the area to be treated, amount of fat tissue, body size, breast size, the presence of bruised or scarred tissue, amount of pericardial fluid, presence of other materials (e.g., sutures) in the intervening tissue, and the location of the target area of the heart 222, particularly the depth of the area relative to the surface of the torso 220. For example, for higher levels of skin pigmentation (with correspondingly higher absorptions), the power density applied to the torso 220 should be higher so as to deliver a predetermined power density of light energy to a selected portion of the heart 222. In addition, the power density selected to be applied to the target area of the patient's heart 222 can depend on other factors, including, but not limited to, the wavelength of the applied light, the type and location of the injury to the heart 222, and the patient's clinical condition.

The target area of the patient's heart 222 to be irradiated can be previously identified by using standard medical imaging techniques. In certain embodiments, treatment includes calculating an initial power density which corresponds to a preselected power density at the target area of the patient's heart 222. The calculation of certain embodiments includes some or all of the factors listed above that affect the penetration of the light energy through the torso 220 and thus the power density at the target area. The power density of light energy to be delivered to the target area of the patient's heart 222 may also be adjusted to be combined with any other therapeutic agent or agents, especially pharmaceutical cardioprotective agents, to achieve the desired biological effect. In such embodiments, the selected power density can also depend on the additional therapeutic agent or agents chosen. The power density and other parameters of the applied light are then adjusted according to the results of the calculation.

These other parameters can include the timing pattern of the phototherapy. In certain embodiments, the light energy is preferably delivered for at least one treatment period of at least about five minutes, and more preferably for at least one treatment period of at least ten minutes. In other embodiments, the treatment proceeds continuously for a period of about 10 seconds to about 2 hours, more preferably for a period of about 1 minute to about 10 minutes, and most preferably for a period of about 1 minute to about 5 minutes.

In certain embodiments, the light energy is pulsed during the treatment period, while in other embodiments, the light energy is continuously applied during the treatment period. If the light is pulsed, the pulse widths are preferably at least about 10 nanoseconds, and are more preferably in a range between approximately 100 microseconds and approximately 20 milliseconds. In certain embodiments, the pulses occur at a frequency of up to about 100 kHz. Continuous wave light may also be used.

In certain embodiments, the treatment may be terminated after one treatment period, while in other embodiments, the treatment may be repeated for at least two treatment periods. The time between subsequent treatment periods is preferably at least about five minutes, more preferably at least about 1 to 2 days, and most preferably at least about one week. In certain embodiments in which treatment is performed over the course of multiple days, the therapy apparatus is wearable over multiple concurrent days. The length of treatment time and frequency of treatment periods can depend on several factors, including the functional recovery of the patient and the results of imaging analysis of the infarct. In certain embodiments, one or more treatment parameters can be adjusted in response to a feedback signal from a device (e.g., electrocardiogram or magnetic resonance imaging) monitoring the patient.

In certain embodiments, the therapy pattern is selected to reduce the amount of scattering and absorption of the light by the lungs during the treatment procedure. Lung tissue surrounds a large fraction of the heart 222 and the lung tissue can be a significant source of scatter and absorption. For example, the lungs are substantially opaque at wavelengths of approximately 810 nanometers. However, during breathing, the lungs move back and forth such that the fraction of the heart 222 occluded from a light source by the lungs varies. Thus, in certain embodiments, irradiation occurs during those portions of the breathing cycle at which the lungs comprise a minimum fraction of the intervening tissue between the light source and the heart 222.

The thrombolytic therapies currently in use for treatment of MI are typically begun within a few hours of the MI. However, many hours often pass before a person who has suffered an MI receives medical treatment, so the short time limit for initiating thrombolytic therapy excludes many patients from treatment. In contrast, phototherapy treatment of MI appears to be more effective if treatment begins no earlier than several hours after the ischemic event has occurred. Consequently, the present methods of phototherapy may be used to treat a greater percentage of MI patients.

In certain embodiments, a method provides a cardioprotective effect in a patient that had an ischemic event in the heart. The method comprises identifying a patient who has experienced an ischemic event in the heart. The method further comprises estimating the time of the ischemic event. The method further comprises commencing administration of a cardioprotective effective amount of light energy to the heart. The administration of the light energy is commenced no earlier than about two hours following the time of the ischemic event. In certain embodiments, phototherapy treatment can be efficaciously performed preferably within 24 hours after the ischemic event occurs, and more preferably no earlier than three hours following the ischemic event, and most preferably no earlier than five hours following the ischemic event. In certain embodiments, one or more of the treatment parameters can be varied depending on the amount of time that has elapsed since the ischemic event.

Without being bound by theory, it is believed that the benefit in delaying treatment occurs because of the time needed for induction of ATP production, and/or the possible induction of angiogenesis in the region surrounding the infarct. Thus, in accordance with one preferred embodiment, the phototherapy for the treatment of MI occurs preferably about 6 to 24 hours after the onset of MI symptoms, more preferably about 12 to 24 hours after the onset of symptoms. It is believed, however, that if treatment begins after about 2 days, its effectiveness will be greatly reduced.

In certain embodiments, the phototherapy is combined with other types of treatments for an improved therapeutic effect. Treatment can comprise directing light through the torso 220 of the patient to a target area of the heart 222 concurrently with applying an electromagnetic field to the heart. In such embodiments, the light has an efficacious power density at the target area and the electromagnetic field has an efficacious field strength. For example, the therapy apparatus can also include systems for electromagnetic treatment, e.g., as described in U.S. Pat. No. 6,042,531 issued to Holcomb, which is incorporated in its entirety by reference herein. In certain embodiments, the electromagnetic field comprises a magnetic field, while in other embodiments, the electromagnetic field comprises a radiofrequency (RF) field. As another example, treatment can comprise directing an efficacious power density of light through the torso 220 of the patient to a target area of the heart 222 concurrently with applying an efficacious amount of ultrasonic energy to the heart 222. Such a system can include systems for ultrasonic treatment, e.g., as described in U.S. Pat. No. 5,054,470 issued to Fry et al., which is incorporated in its entirety by reference herein.

Directing Light Onto Cardiac Tissue: Therapy Apparatus Control

Figure 15:
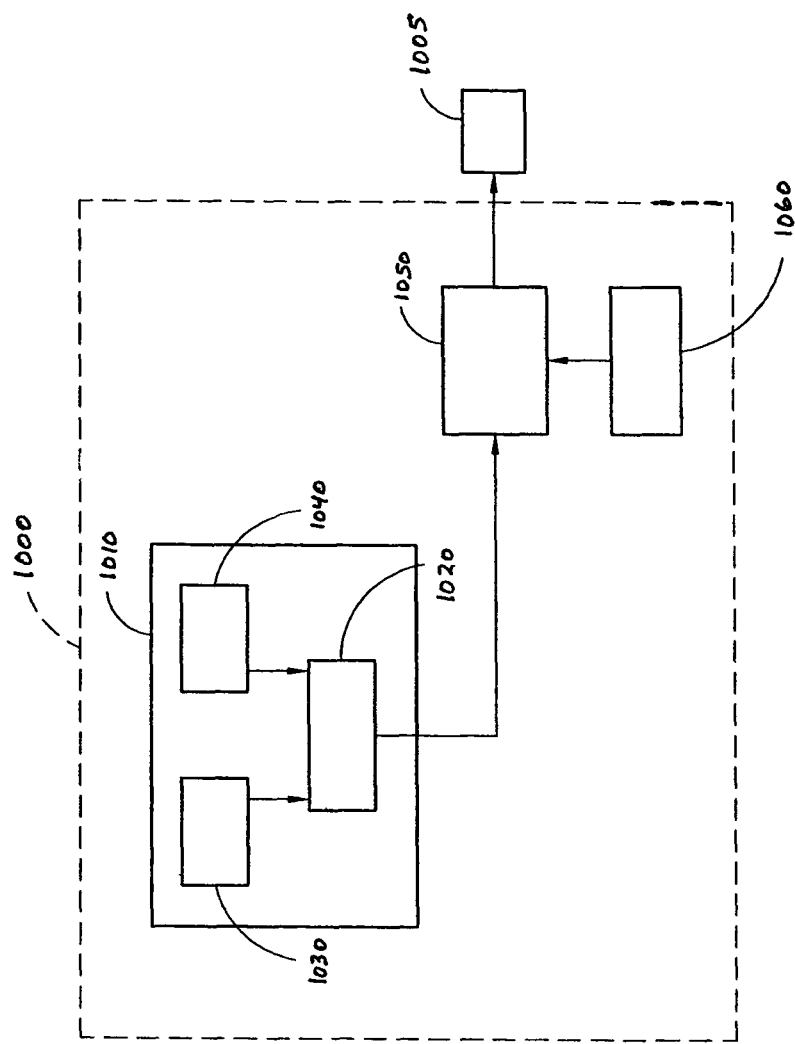
FIG. 15 is a block diagram of a control circuit comprising a programmable controller.

FIG. 15 is a block diagram of a control circuit 1000 comprising a programmable controller 1010 coupled to a light source 1005 according to embodiments described herein. The control circuit 1000 is configured to adjust the power of the light energy emitted by the light source 1005 to generate a predetermined energy delivery profile, such as a predetermined subsurface power density, to the target area of the heart 222. In certain embodiments, the control circuit 1000 is also configured to adjust other parameters of the phototherapy, including but not limited to, pulsing of the light, number, frequency, and duration of treatment periods, pattern of irradiation applied to the patient, wavelengths of the light, and the magnitude, timing, and duration of the application of other sources of energy (e.g., magnetic, RF, ultrasonic) to the heart.

In certain embodiments, the programmable controller 1010 comprises a logic circuit 1020, a clock 1030 coupled to the logic circuit 1020, and an interface 1040 coupled to the logic circuit 1020. The clock 1030 of certain embodiments provides a timing signal to the logic circuit 1020 so that the logic circuit 1020 can monitor and control timing intervals of the applied light. Examples of timing intervals include, but are not limited to, total treatment times, pulsewidth times for pulses of applied light, and time intervals between pulses of applied light. In certain embodiments, the light source 1005 can be selectively turned on and off to reduce the thermal load at the torso 220 and to deliver a selected power density to the target cardiac tissue. In addition, in embodiments using a plurality of light sources, the light sources can be selectively activated to provide a predetermined pattern of irradiation.

The interface 1040 of certain embodiments provides signals to the logic circuit 1020 which the logic circuit 1020 uses to control the applied light. The interface 1040 can comprise a user interface or an interface to a sensor monitoring at least one parameter of the treatment. In certain such embodiments, the programmable controller 1010 is responsive to signals from the sensor to preferably adjust the treatment parameters to optimize the measured response. The programmable controller 1010 can thus provide closed-loop monitoring and adjustment of various treatment parameters to optimize the phototherapy. The signals provided by the interface 1040 from a user are indicative of parameters that may include, but are not limited to, patient characteristics (e.g., skin type, fat percentage), selected applied power densities, target time intervals, and power density/timing profiles for the applied light.

In certain embodiments, the logic circuit 1020 is coupled to a light source driver 1050. The light source driver 1050 is coupled to a power supply 1060, which in certain embodiments comprises a battery and in other embodiments comprises an alternating current source. The light source driver 1050 is also coupled to the light source 1005. The logic circuit 1020 is responsive to the signal from the clock 1030 and to user input from the user interface 1040 to transmit a control signal to the light source driver 1050. In response to the control signal from the logic circuit 1020, the light source driver 1050 adjust and controls the power applied to the light source 1005. Other control circuits besides the control circuit 1000 of FIG. 15 are compatible with embodiments described herein.

In certain embodiments, the logic circuit 1020 is responsive to signals from a sensor monitoring at least one parameter of the treatment to control the applied light. For example, certain embodiments comprise a temperature sensor thermally coupled to the torso 220 to provide information regarding the temperature of the torso 220 to the logic circuit 1020. In such embodiments, the logic circuit 1020 is responsive to the information from the temperature sensor to transmit a control signal to the light source driver 1050 so as to adjust the parameters of the applied light to maintain the temperature at the torso 220 below a predetermined level. Other embodiments include exemplary biomedical sensors including, but not limited to, an electrocardiograph sensor, a blood flow sensor, a blood gas (e.g., oxygenation) sensor, an ATP production sensor, or a cellular activity sensor. Such biomedical sensors can provide real-time feedback information to the logic circuit 1020. In certain such embodiments, the logic circuit 1020 is responsive to signals from the sensors to preferably adjust the parameters of the applied light to optimize the measured response. The logic circuit 1020 can thus provide closed-loop monitoring and adjustment of various parameters of the applied light to optimize the phototherapy.

Example: Phototherapy on Neurons

While the following description recounts the irradiation of neurons with an efficacious power density of light, it serves as an example of the phototherapy technique in general. An in vitro experiment was done to demonstrate one effect of phototherapy on neurons, namely the effect on ATP production. Normal Human Neural Progenitor (NHNP) cells were obtained cryopreserved through Clonetics of Baltimore, Md., catalog # CC-2599. The NHNP cells were thawed and cultured on polyethyleneimine (PEI) with reagents provided with the cells, following the manufacturers' instructions. The cells were plated into 96 well plates (black plastic with clear bottoms, Becton Dickinson of Franklin Lakes, N.J.) as spheroids and allowed to differentiate into mature neurons over a period of two weeks.

A Photo Dosing Assembly (PDA) was used to provide precisely metered doses of laser light to the NHNP cells in the 96 well plates. The PDA included a Nikon Diaphot inverted microscope (Nikon of Melville, N.Y.) with a LUDL motorized x,y,z stage (Ludl Electronic Products of Hawthorne, N.Y.). An 808 nanometer laser was routed into the rear epi-fluorescent port on the microscope using a custom designed adapter and a fiber optic cable. Diffusing lenses were mounted in the path of the beam to create a "speckled" pattern, which was intended to mimic in vivo conditions after a laser beam passed through human skin. The beam diverged to a 25 millimeter diameter circle when it reached the bottom of the 96 well plates. This dimension was chosen so that a cluster of four adjacent wells could be lased at the same time. Cells were plated in a pattern such that a total of 12 clusters could be lased per 96 well plate. Stage positioning was controlled by a Silicon Graphics workstation and laser timing was performed by hand using a digital timer. The measured power density passing through the plate for the NHNP cells was 50 mW/cm$^2$.

Two independent assays were used to measure the effects of 808 nanometer laser light on the NHNP cells. The first was the CellTiter-Glo Luminescent Cell Viability Assay (Promega of Madison, Wis.). This assay generates a "glow-type" luminescent signal produced by a luciferase reaction with cellular ATP. The CellTiter-Glo reagent is added in an amount equal to the volume of media in the well and results in cell lysis followed by a sustained luminescent reaction that was measured using a Reporter luminometer (Turner Biosystems of Sunnyvale, Calif.). Amounts of ATP present in the NHNP cells were quantified in Relative Luminescent Units (RLUs) by the luminometer.

The second assay used was the alamarBlue assay (Biosource of Camarillo, Calif.). The internal environment of a proliferating cell is more reduced than that of a non-proliferating cell. Specifically, the ratios of NADPH/NADP, FADH/FAD, FMNH/FMN and NADH/NAD, increase during proliferation. Laser irradiation is also thought to have an effect on these ratios. Compounds such as alamarBlue are reduced by these metabolic intermediates and can be used to monitor cellular states. The oxidization of alamarBlue is accompanied by a measurable shift in color. In its unoxidized state, alamarBlue appears blue; when oxidized, the color changes to red. To quantify this shift, a 340PC microplate reading spectrophotometer (Molecular Devices of Sunnyvale, Calif.) was used to measure the absorbance of a well containing NHNP cells, media and alamarBlue diluted 10% v/v. The absorbance of each well was measured at 570 nanometers and 600 nanometers and the percent reduction of alamarBlue was calculated using an equation provided by the manufacturer.

The two metrics described above, (RLUs and % Reduction) were then used to compare NHNP culture wells that had been lased with 50 mW/cm$^2$ at a wavelength of 808 nanometers. For the CellTiter-Glo assay, 20 wells were lased for 1 second and compared to an unlased control group of 20 wells. The CellTiter-Glo reagent was added 10 minutes after lasing completed and the plate was read after the cells had lysed and the luciferase reaction had stabilized. The average RLUs measured for the control wells was 3808+/−3394 while the laser group showed a two-fold increase in ATP content to 7513+/−6109. The standard deviations were somewhat high due to the relatively small number of NHNP cells in the wells (approximately 100 per well from visual observation), but a student's unpaired t-test was performed on the data with a resulting p-value of 0.02 indicating that the two-fold change is statistically significant.

The alamarBlue assay was performed with a higher cell density and a lasing time of 5 seconds. The plating density (calculated to be between 7,500-26,000 cells per well based on the certificate of analysis provided by the manufacturer) was difficult to determine since some of the cells had remained in the spheroids and had not completely differentiated. Wells from the same plate can still be compared though, since plating conditions were identical. The alamarBlue was added immediately after lasing and the absorbance was measured 9.5 hours later. The average measured values for percent reduction were 22%+/−7.3% for the 8 lased wells and 12.4%+/−5.9% for the 3 unlased control wells (p-value=0.076). These alamarBlue results support the earlier findings in that they show a similar positive effect of the laser treatment on the cells.

Increases in cellular ATP concentration and a more reduced state within the cell are both related to cellular metabolism and are considered to be indications that the cell is viable and healthy. These results are novel and significant in that they show the positive effects of laser irradiation on cellular metabolism in in-vitro neuronal cell cultures.

The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention.

What is claimed is:

1. A method of treating a patient's heart, the method comprising:
    providing a therapy apparatus that emits light having a controllably variable power density, the therapy apparatus comprising a plurality of light sources and defining two or more groups of the light sources, each of the defined groups of the light sources comprising two or more of the light sources from the plurality of light sources that are configured to be selectively activated together as a group;

positioning the therapy apparatus relative to the patient's heart with intervening tissue including lung tissue of the patient between the plurality of light sources and the patient's heart; and selectively activating two or more of the groups of the light sources in manners that differ in comparison to each other and directing light emitted from the two or more of the groups of the light sources onto cardiac tissue of the patient's heart through the intervening tissue without damaging the intervening tissue, wherein the light emitted from the two or more groups of the light sources is simultaneously activated during the patient's breathing cycle to provide a therapy pattern, and wherein the light is directed onto the cardiac tissue during selected portions of the patient's breathing cycle during which a percentage of the intervening lung tissue is at a minimum.

2. The method of claim 1, wherein the two or more of the groups of the light sources emit light having an initial power density of at least 10 mW/cm$^2$ during the selected portions of the patient's breathing cycle.

3. The method of claim 1, wherein the two or more of the groups of the light sources emit light having an initial power density between 10 mW/cm$^2$ and 10 W/cm$^2$ during the selected portions of the patient's breathing cycle.

4. The method of claim 1, wherein the light has a wavelength between 590 nanometers and 3000 nanometers.

5. The method of claim 1, wherein the light has a wavelength between 780 nanometers and 1064 nanometers.

6. The method of claim 1, wherein the light has a wavelength between 780 nanometers and 840 nanometers.

7. The method of claim 1, wherein the light comprises a first wavelength and light having a second wavelength, the light having the first wavelength being transmitted concurrently with the light having the second wavelength to the cardiac tissue.

8. The method of claim 1, wherein the light emitted by the two or more of the groups of the light sources is pulsed.

9. The method of claim 1, wherein positioning the plurality of light sources comprises placing the plurality of light sources outside the patient's torso and interposing an element between the plurality of light sources and the torso, the element inhibiting temperature increases at the torso due to the light.

10. The method of claim 1, wherein positioning the therapy apparatus comprises placing the therapy apparatus on the patient's skin surface.

11. The method of claim 1, wherein the plurality of light sources comprises at least one needle which provides a conduit for the light from the plurality of light sources, and positioning the plurality of light sources comprises inserting the at least one needle through at least a portion of the skin of the patient's torso.

12. The method of claim 1, further comprising directing the light onto the cardiac tissue for at least one treatment period of at least ten minutes.

13. The method of claim 1, further comprising directing the light onto the cardiac tissue for at least one treatment period of at least five minutes.

14. The method of claim 1, further comprising directing the light onto the cardiac tissue for a first treatment period and for a second treatment period commenced subsequent to the completion of the first treatment period.

15. The method of claim 14, wherein commencement of the second treatment period occurs at least five minutes after completion of the first treatment period.

16. The method of claim 14, wherein commencement of the second treatment period occurs at least one week after completion of the first treatment period.

17. The method of claim 1, wherein the directing light onto the cardiac tissue comprises pulsing the light such that the light is directed onto the cardiac tissue only during the selected portions of the patient's breathing cycle during which the percentage of the intervening lung tissue is at the minimum.

18. The method of claim 1, wherein the cardiac tissue is irradiated by an average power density of at least 0.01 mW/cm$^2$ during the selected portions of the patient's breathing cycle.

19. A method for treating a patient's heart, the method comprising:

introducing light onto a target area of the heart by directing the light having a controllably variable power density through intervening tissue of the patient without damaging the intervening tissue, wherein the light is from a therapy apparatus comprising a plurality of light sources and defining two or more groups of the light sources, each of the defined groups of the light sources comprising two or more of the light sources from the plurality of light sources that are configured to be selectively activated together as a group, wherein the light emitted from the two or more groups of the light sources is simultaneously activated during the patient's breathing cycle to provide a therapy pattern such that the light impinges onto the target area during selected portions of the patient's breathing cycle, and wherein the light is introduced from the plurality of light sources positioned within the patient's esophagus.

20. The method of claim 19, wherein the light comprises a first wavelength and light having a second wavelength, the light having the first wavelength being transmitted sequentially with the light having the second wavelength to the target area of the heart.

21. The method of claim 19, further comprising determining the initial power density to be introduced so as to deliver the efficacious power density onto the target area, said determining based on at least one characteristic indicative of attenuation of light by the intervening tissue.

22. The method of claim 21, wherein the characteristic is selected from a group consisting of: skin pigmentation, presence and color of hair over the target area, amount of fat tissue, body size, breast size, presence of bruised or scarred tissue, amount of pericardial fluid, presence of other materials within the intervening tissue, and the location of the target area of the heart.

23. The method of claim 19, wherein the directing light comprises pulsing the light such that the light is directed onto the cardiac tissue only during the selected portions of the patient's breathing cycle during which lung tissue comprises a minimum fraction of the intervening tissue.

24. The method of claim 19, wherein the light has an initial power density of at least 10 mW/cm$^2$ during the selected portions of the patient's breathing cycle.

25. The method of claim 19, wherein the light has an initial power density between 10 mW/cm$^2$ and 10 W/cm$^2$ during the selected portions of the patient's breathing cycle.

26. The method of claim 19, wherein the target area is irradiated by an average power density of at least 0.01 mW/cm² during the selected portions of the patient's breathing cycle.

27. A method of treating a patient's heart, the method comprising:
positioning a therapy apparatus comprising a plurality of light sources and defining two or more groups of the light sources, each of the defined groups of the light sources comprising two or more of the light sources from the plurality of light sources that are configured to be selectively activated together as a group, the groups of the light sources having a controllably variable power density relative to the patient's heart with intervening tissue including lungs of the patient between the plurality of light sources and the patient's heart; and
directing light onto cardiac tissue of the patient's heart from the plurality of light sources through the intervening tissue without damaging the intervening tissue, the light emitted from the two or more groups of the light sources being simultaneously activated during the patient's breathing cycle to provide a therapy pattern during selected portions of the patient's breathing cycle during which a percentage of the intervening lung tissue is at a minimum.

28. The method of claim 27, wherein the cardiac tissue is irradiated by an average power density of light of at least 0.01 mW/cm².

29. The method of claim 27, wherein the directing light onto the cardiac tissue comprises pulsing the light such that the light is directed onto the cardiac tissue only during the selected portions of the patient's breathing cycle during which the percentage of the intervening lung tissue is at the minimum.

30. The method of claim 27, wherein the light source emits light having an initial power density of at least 10 mW/cm² during the selected portions of the patient's breathing cycle.

31. The method of claim 27, wherein the light source emits light having an initial power density between 10 mW/cm² and 10 W/cm² during the selected portions of the patient's breathing cycle.

* * * * *